(12) United States Patent
Bauer et al.

(10) Patent No.: US 11,458,301 B2
(45) Date of Patent: Oct. 4, 2022

(54) FIXATION DEVICE FOR MEDICAL DEVICE RETENTION

(71) Applicant: Medtronic, Inc., Minneapolis, MN (US)

(72) Inventors: Ryan T. Bauer, Plymouth, MN (US); Phillip C. Falkner, Minneapolis, MN (US); Randy S. Roles, Elk River, MN (US); Elizabeth Kregel, Robbinsdale, MN (US)

(73) Assignee: Medtronic, Inc., Minneapolis, MN (US)

( * ) Notice: Subject to any disclaimer, the term of this patent is extended or adjusted under 35 U.S.C. 154(b) by 66 days.

(21) Appl. No.: 16/402,364

(22) Filed: May 3, 2019

(65) Prior Publication Data

US 2019/0336752 A1 Nov. 7, 2019

Related U.S. Application Data

(60) Provisional application No. 62/667,109, filed on May 4, 2018.

(51) Int. Cl.
*A61N 1/05* (2006.01)
*A61N 1/36* (2006.01)
*A61N 1/375* (2006.01)

(52) U.S. Cl.
CPC ......... *A61N 1/0539* (2013.01); *A61N 1/0504* (2013.01); *A61N 1/0534* (2013.01); *A61N 1/3605* (2013.01); *A61N 1/375* (2013.01)

(58) Field of Classification Search
CPC .. A61N 1/0539; A61N 1/0534; A61N 1/3605; A61N 1/375
See application file for complete search history.

(56) References Cited

U.S. PATENT DOCUMENTS

| | | | |
|---|---|---|---|
| 2012/0289964 A1* | 11/2012 | Nakaji | A61B 17/688 606/80 |
| 2013/0123841 A1 | 5/2013 | Lyon | |
| 2014/0194907 A1* | 7/2014 | Bonutti | A61F 2/0811 606/151 |
| 2017/0189676 A1* | 7/2017 | Bentley | A61N 1/0558 |
| 2017/0238981 A1* | 8/2017 | Madjarov | A61B 17/8085 |
| 2019/0099597 A1* | 4/2019 | Mirro | A61B 90/11 |

OTHER PUBLICATIONS

Slone et al., "Orthopedic Fixation Devices," Radio Graphics, Jun. 13, 1991, 25 pp.

* cited by examiner

*Primary Examiner* — Lynsey C Eiseman
*Assistant Examiner* — Jessica L Mullins
(74) *Attorney, Agent, or Firm* — Shumaker & Sieffert, P.A.

(57) ABSTRACT

In some examples, a fixation device includes a flexible band with a first base portion, a second base portion, and a connecting strap connecting the first base portion to the second base portion, the connecting strap configured to retain a medical device to an anatomical structure of a patient, wherein the flexible band is constructed of a first material. The fixation device may further include a plurality of inserts, each insert of the plurality of inserts defining an inner channel and constructed of a second material more rigid than the first material of the flexible band, wherein a first insert of the plurality of inserts is at least partially within the first base portion, and wherein a second insert of the plurality of inserts is at least partially within the second base portion.

22 Claims, 38 Drawing Sheets

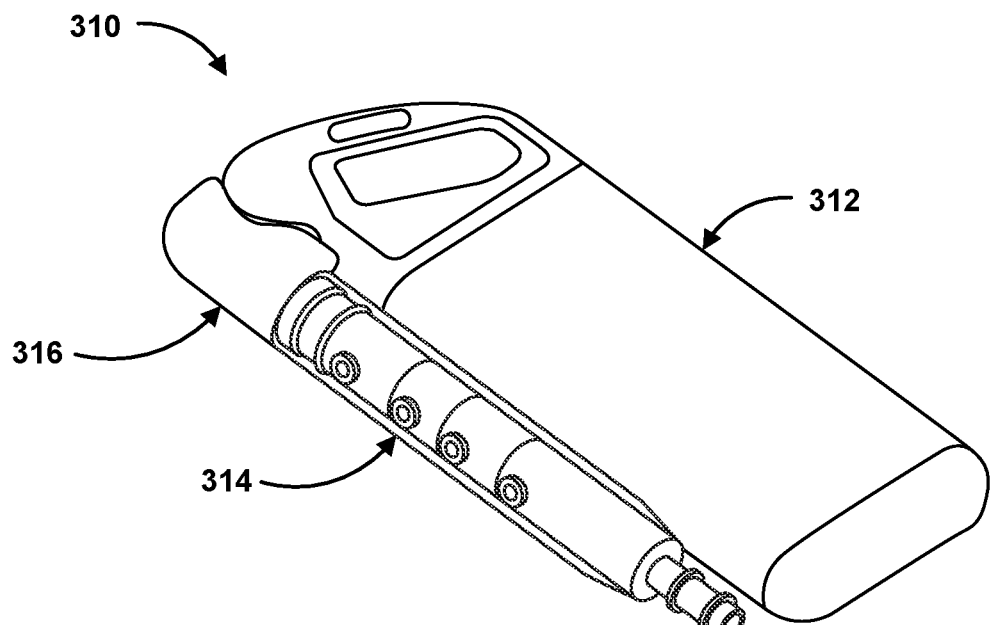
FIG. 14A
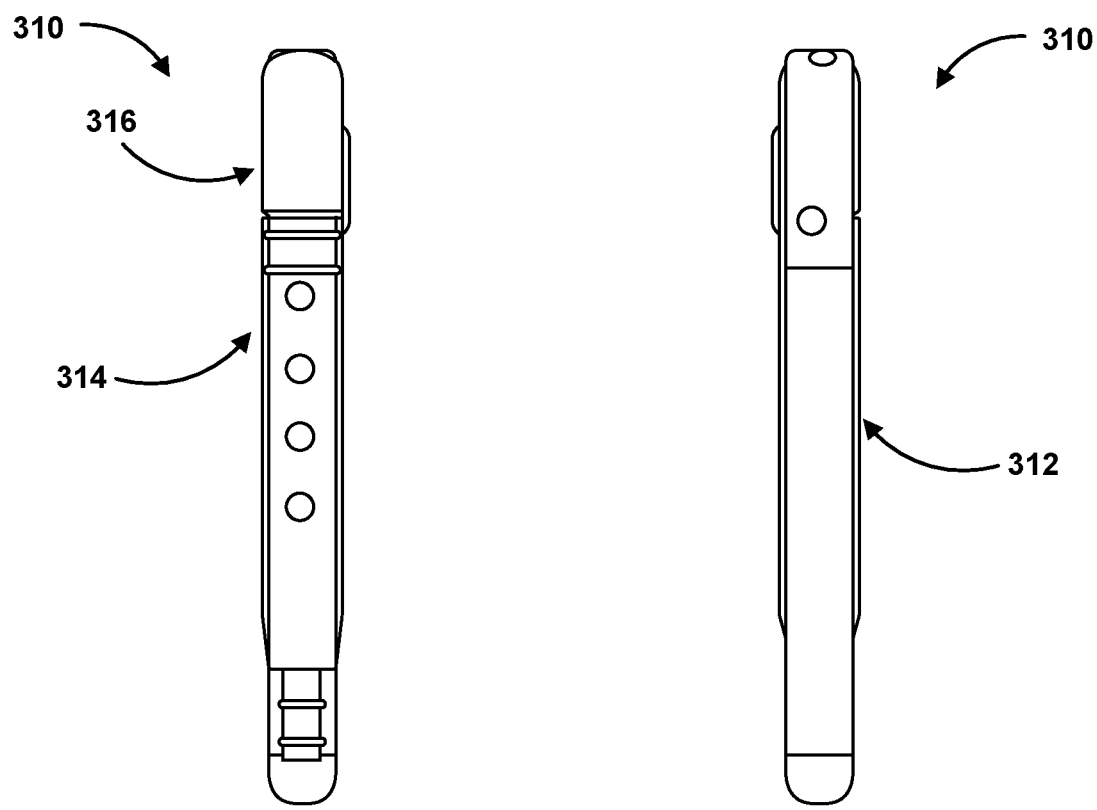
FIG. 14B
FIG. 14C

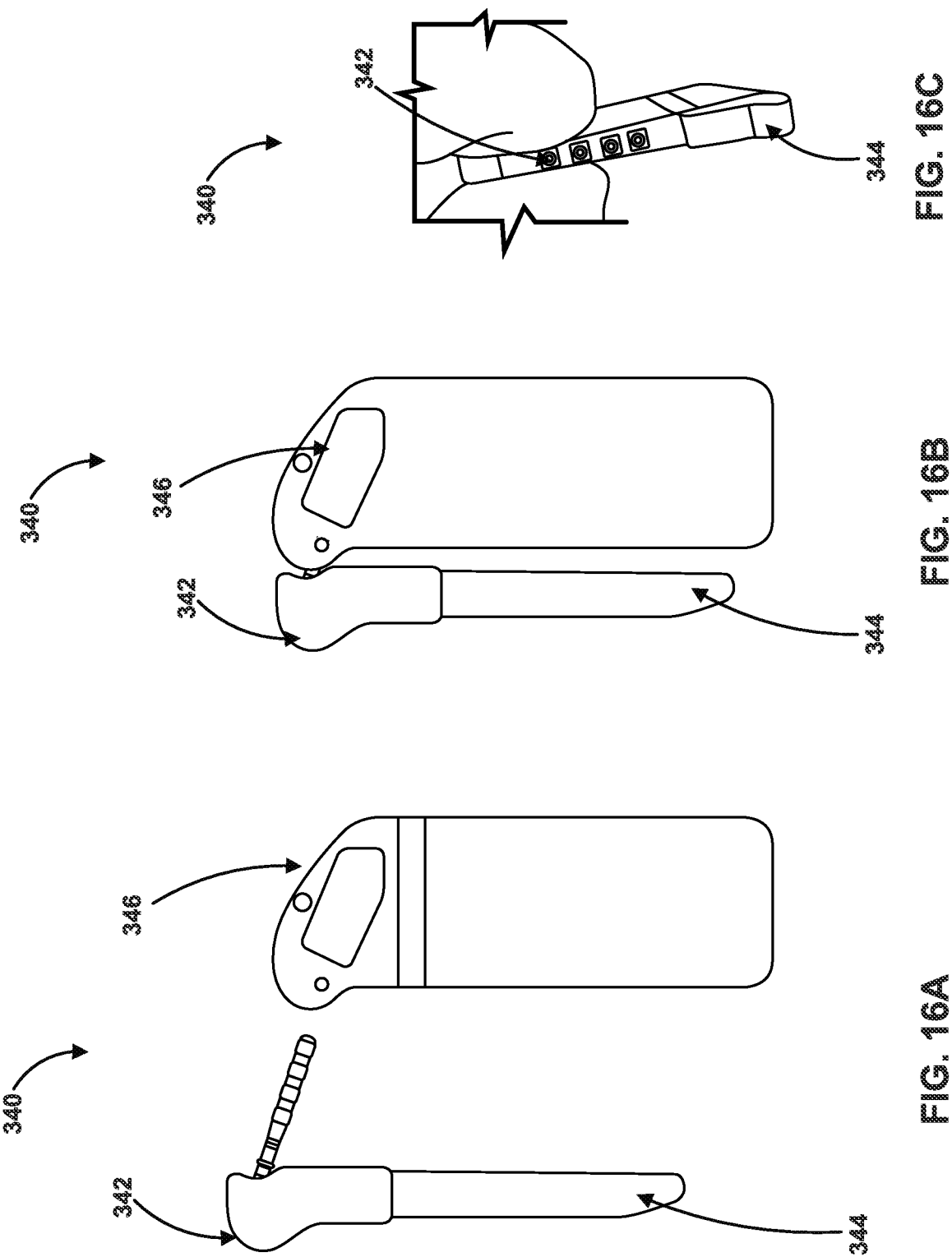

ured to retain a medical device to an anatomical structure of a
FIXATION DEVICE FOR MEDICAL DEVICE RETENTION This application claims the benefit of U.S. Provisional Patent Application No. 62/667,109, filed on May 4, 2018, the entire contents of which is incorporated by reference herein.

FIELD

The disclosure relates to a fixation device configured to secure a medical device to tissue of a patient.

BACKGROUND

Medical devices may be external or implanted. Some implanted medical devices may be secured within a subcutaneous pocket created by a clinician. Other implanted medical devices may be positioned within or under layers of muscle. In other examples, bone screws may be used to secure a medical device to a bone, such as the cranium of the patient.

SUMMARY

This disclosure is directed to fixation devices configured to fix or secure medical devices to bone of a patient, such as a portion of a cranium of the patient. In order to secure a medical device, such as an implantable neurostimulator (INS), to a cranium of patient, a fixation device may be disposed over a portion of the medical device and secured to the cranium of a patient. For example, the fixation device may be secured to the cranium at either sides of the medical device and stretched over the INS to provide a bias force against the INS. In some examples, a portion of the patient's cranium may be removed to create a cranium recess to accommodate at least a portion of the medical device. A stretchable fixation device may be configured to secure medical devices of varying sizes that may protrude varying heights from the surface of the cranium and span cranium recesses of varying sizes in the cranium of the patient.

In some examples, the fixation device may include an insert on at least one end of the fixation device. The insert may provide a channel configured to accept an attachment mechanism, such as a bone screw, to be inserted through the insert to secure the fixation device to the cranium. The insert may provide a rigid structure that supports the force created by the attachment device. The fixation device may be constructed of a material, such as a polymer, that does not interfere with, or interact with, communication signals or charging energy transmitted from an external device to the medical device secured by the fixation device.

In some examples, the disclosure describes a fixation device that may include a flexible band with a first base portion, a second base portion, and a connecting strap connecting the first base portion to the second base portion, the connecting strap configured to retain a medical device to an anatomical structure of a patient, wherein the flexible band is constructed of a first material. The fixation device may further include a plurality of inserts, each insert of the plurality of inserts defining an inner channel and constructed of a second material more rigid than the first material of the flexible band, wherein a first insert of the plurality of inserts is at least partially within the first base portion, and wherein a second insert of the plurality of inserts is at least partially within the second base portion.

In some examples, the disclosure describes a fixation system comprising fixation device that may include a flexible band with a first base portion, a second base portion, and a connecting strap connecting the first base portion to the second base portion, the connecting strap configured to retain a medical device to an anatomical structure of a patient, wherein the flexible band is constructed of a first material. The fixation device may further include a plurality of inserts, each insert of the plurality of inserts defining an inner channel and constructed of a second material more rigid than the first material of the flexible band, wherein a first insert of the plurality of inserts is at least partially within the first base portion, and wherein a second insert of the plurality of inserts is at least partially within the second base portion. The fixation system may further include at least one attachment mechanism configured to attach the fixation device to a patient.

In some examples, the disclosure describes a method placing a medical device on a patient and extending a fixation device over the medical device. The fixation device may include a flexible band with a first base portion, a second base portion, and a connecting strap connecting the first base portion to the second base portion, the connecting strap configured to retain a medical device to an anatomical structure of a patient, wherein the flexible band is constructed of a first material. The fixation device may further include a plurality of inserts, each insert of the plurality of inserts defining an inner channel and constructed of a second material more rigid than the first material of the flexible band, wherein a first insert of the plurality of inserts is at least partially within the first base portion, and wherein a second insert of the plurality of inserts is at least partially within the second base portion. The method may further include securing the fixation device to the patient.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 14A, 14B, 14C, 14D, 14E, and 14F are conceptual diagrams illustrating an example medical system, in accordance with one or more aspects of this disclosure.

FIGS. 16A, 16B, and 16C are conceptual diagrams illustrating an example medical system, in accordance with one or more aspects of this disclosure.

DETAILED DESCRIPTION

Figure 1A:
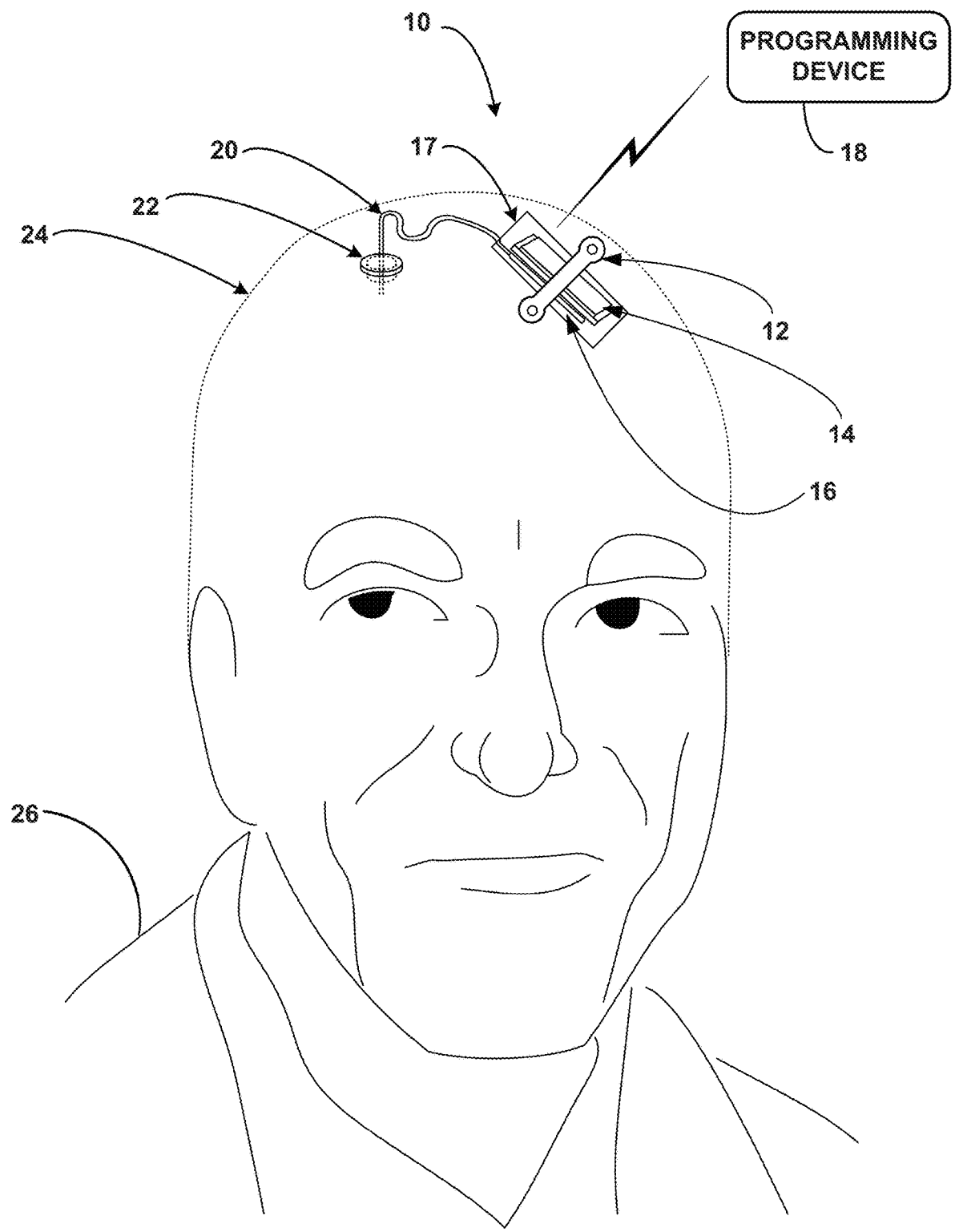
FIG. 1A is a conceptual diagram illustrating an example medical system, in accordance with one or more aspects of this disclosure.

In general, this disclosure is directed to devices, systems, and techniques for securing a medical device to a patient. For example, a fixation device may be configured to attach to a cranium of the patient to retain a medical device, such as an implantable medical device (IMD). In order to treat certain diseases or disorders, an elongated member, such as an electrical stimulation lead or a drug delivery catheter, may be implanted within the cranium of a patient. Typically, the elongated member is positioned to reach a target location within the brain, pass through a burr hole created in the cranium, and be coupled to a medical device outside of the cranium. Some medical devices may rest on an exterior of the patient, and other medical devices may be partially or fully inserted within a patient. An IMD, which may include an implantable neurostimulator (INS) in some examples, may be implanted in a pocket below the pectorals with a lead extending to the cranium and inserted into the brain of a patient. The pocket below the pectoral may provide a secure location for the IMD so that it does not become dislodged from the patient. In addition, the pocket below the pectoral may also accommodate a relatively large IMD without restricting patient activity.

However, a lead that is implanted along the length of neck of the patient may be subject to integrity issues. Due to years of neck, and lead, flexing with movement of the patient may cause wear and tear on the lead. This wear and tear may result in lead damage such as conductor fracture. In addition, a patient may have reduced mobility by trying to preserve the integrity of the lead by reducing or eliminating activities that may compromise the integrity of the lead. Furthermore, longer leads may increase power consumption by the IMD and lead to decreased battery longevity or more frequent recharge sessions.

In some cases, as medical devices become smaller, medical devices may be located at other locations of the patient. For example, smaller medical devices may be moved to smaller pockets within the human body or moved to the exterior surface of the body, e.g., the exterior surface of the cranium. In some cases, a need may exist to secure the medical device without damaging the medical device or causing harm to the patient. Moreover, typical methods of securing medical devices at these locations may interfere with the operation of the medical device or present other issues for the patient. For example, a metal bracket used to secure a medical device may interfere with communication signals or charging energy sent to the medical device. As another example, an electrical field generated for inductive charging of the medical device may generate eddy currents within the metal bracket that increases the temperature of the metal bracket to unacceptable levels for the patient.

As described herein, systems, devices, and techniques are directed to one or more fixation devices configured to secure a medical device to a cranium of a patient. For example, a fixation device may be configured to be flexible and elastic such that the fixation device may be stretched over a medical device to be at least partially implanted in the cranium of the patient. In some examples, the fixation device may include at least one insert within the fixation device configured to be more rigid than the elastic fixation device. The insert may thus be configured to receive an attachment mechanism, such as a bone screw, for securing the fixation device to the cranium of the patient. The fixation device may be configured to enable securing the medical device to the cranium while the medical device is recessed from the external surface of the cranium, flush with the external surface of the cranium, or extended beyond the external surface of the cranium. By securing the medical device, the fixation device may prevent movement of the medical device with respect to the cranium, such as movement away from the cranium and/or along the surface of the cranium. The fixation device may be configured to maintain a medical device fully inserted in a patient from moving to a position where the medical device protrudes to the exterior of the patient.

In some examples, a clinician, such as a physician, nurse, or other medical professional, may stretch the fixation device over a medical device to provide a bias against the medical device. After stretching the fixation device, the clinician may secure the fixation device to the patient by an attachment mechanism. For example, the attachment mechanism may include one or more of a bone screw, a nut, a washer, a wire, a pin, a nail, bone cement, or a staple. In some examples, a clinician may use more than one fixation device to secure the medical device to the patient.

As described in examples herein, an IMD may be placed on top of the cranium, or at least partially within the cranium, of the patient. Placement of the IMD on the cranium may enable shorter lead lengths for leads entering the cranium than would otherwise be possible when implanting the IMD below the clavicle of the patient. Lead stretch and conductor fracture within the lead may be reduced when the lead does not need to traverse the patient's neck. In some examples, the fixation device may be constructed of non-metallic (e.g., not electrically conductive) materials. For example, a fixation device may be constructed of a polymer. Since the fixation device is not electrically conductive, the fixation device may not generate eddy currents, and associated heating, during inductive charging of the IMD from an external charging device. In addition, nonmetallic materials used to construct the fixation device may reduce the potential for interference with communication signals transmitted to IMD from an external charging device and/or external programming device.

In some examples, the fixation device may comprise a shape that is configured to be substantially flush with the cranium of the patient, or limit any additional thickness beyond the IMD. The shape of the fixation device may be formed to match the dimensions of a specific cranium recess of the patient and/or constructed of a material that is elastic, and/or flexible, to form to the curvature of the cranium and extend over the IMD. In some examples, the exterior surface of the fixation device may have a low-profile such that the fixation device does not extend substantially further from the cranium than the height of the IMD.

In some examples, a single fixation device may be used across a variety of medical situations. For examples, a single fixation device may be used to retain an IMD that remains flush with the cranium, remains recessed and does not reach the surface of the cranium, or extends for a height past the cranium. Consequently, a clinician may need access to fewer different fixation devices during a medical procedure to secure the IMD to the cranium or other location. In other examples, a plurality of fixation devices may be used at a single time to secure a single IMD. The plurality of fixation devices may provide additional retaining force, increase the coefficient of friction with the IMD, and/or cover a greater surface area of the IMD. For example, by securing three fixation devices over the IMD, the three fixation devices may prevent the IMD from being dislodged by powerful and/or repeated hits and may prevent the IMD from repositioning within the cranium recess.

Although the fixation device and techniques herein are described with respect to securing a medical device to a cranium, these fixation devices and techniques may be utilized at any anatomical location in which a medical device needs to be secured to bone or other substantially rigid tissue.

FIG. 1A is a conceptual diagram illustrating an example medical system 10, in accordance with one or more aspects of this disclosure. In the example of FIG. 1A, system 10 includes a fixation device 12, an implantable medical device (IMD) 14, an adaptor 16, a programming device 18, and a lead 20. IMD 14 is disposed within cranium recess 17 and attached to cranium 24, and lead 20 passes through burr hole 22 in cranium 24 of patient 26. By extending fixation device 12 over a portion of IMD 14, fixation device 12 may secure IMD 14 to cranium 24 and within cranium recess 17. When attached to cranium 24, fixation device 12 may reduce the likelihood that IMD 14 moves with respect to cranium 24 or pulls on lead 20—actions which may dislodge lead 20 from a target site within cranium 24. Consequently, fixation device 12 may enable lead 20 and IMD 14 to provide consistent treatment to patient 26 without interruption due to IMD 14 or lead 20 becoming dislodged.

Although the techniques described in this disclosure are generally applicable to a variety of medical devices, this disclosure generally discusses techniques in the context of fixation devices securing or restraining an IMD, such as an INS, coupled to electrical stimulation leads for delivering deep brain stimulation (DBS) therapy. However, this disclosure may refer to a fixation device that may be used for many types of leads, medical devices, and therapies. For example, therapies may include electrical stimulation therapy to various tissue sites to treat a variety of symptoms or conditions such as chronic pain, tremors, Parkinson's disease, epilepsy, urinary or fecal incontinence, sexual dysfunction, obesity, or gastroparesis. Electrical stimulation may be used in different therapeutic applications, such as spinal cord stimulation (SCS), pelvic stimulation, gastric stimulation, or peripheral nerve field stimulation (PNFS). Fixation device 12 may be a flexible band used to restrain a variety of IMDs that have different shapes, sizes, and/or functions. For example, fixation device 12 may extend over lead 20 and restrain lead 20 to cranium 24 to secure IMD 14 to cranium 24. In other examples, fixation device 12 may be configured to secure elongated members such as leads carrying temperature sensors, ultrasound transducers, or cameras, or elongated members defining one or more lumens such as a drug delivery catheter.

Fixation device 12 may be configured to be secured anywhere on cranium 24 that is appropriate for insertion or placement of IMD 14. In the example of FIG. 1A, a clinician may remove part of cranium 24 to make cranium recess 17 with dimensions appropriate for receiving IMD 14, such as an appropriate depth, width, height, or shape, depending on the dimensions of IMD 14. If IMD 14 is implanted within cranium recess 17, fixation device 12 may be secured to cranium 24 at a location outside of cranium recess 17. For example, if cranium recess 17 is in the shape of a rectangle (e.g., to accommodate a rectangularly shaped IMD 14), fixation device 12 may be configured to extend over cranium recess 17 in a longitudinal, lateral, and/or oblique direction with respect to cranium recess 17. In some examples, cranium recess 17 may reduce or eliminate the distance IMD 14 protrudes from the exterior surface of cranium 24. In addition, cranium recess 17 may reduce the risk of IMD 14 migrating across the surface of cranium 24 under the scalp. In other examples, fixation device 12 may be attached to cranium 24 to secure IMD 14 against the exterior surface of cranium 24 without being inserted into cranium recess 17. When fixation device 12 is extended over IMD 14, fixation device 12 may be stretched in some examples. In other words, fixation device 12 may be configured to have an elasticity that enables fixation device 12 to be elongated, or strained, when disposed over IMD 14 as compared to the resting length of fixation device 12 prior to attachment. Fixation device 12 may be configured to such that only certain portions of fixation device 12 have elasticity to stretch and/or enable stretch in a certain direction. For example, one or more portions of fixation device 12 may have a smaller cross-sectional area than other portions of fixation device 12 to promote elongation along those portions of fixation device 12 having the smaller cross-sectional areas. Put another way, a smaller cross-sectional area of fixation device 12 may allow more strain to a tensile force than a larger cross-sectional area constructed of the same material.

In some examples, fixation device 12 may be formed of materials configured to retain IMD 14 for as long as IMD 14 remains on patient 26. IMD 14 and lead 20 may remain implanted within patient 26 for weeks, months, or years. Consequently, fixation device 12 may be configured to remain secured to cranium 24 and retain IMD 14 for the same amount of time. In some examples, fixation device 12 may be constructed of a material that is biocompatible with patient 26 for these durations. In other examples, fixation device 12 may be configured to biodegrade over time because tissue growth around IMD 14 may encapsulate IMD 14 and reduce or eliminate the need for fixation device 12 to secure IMD 14. Fixation device 12 may be constructed of any polymer, metal, or composite material suitable for being implanted within patient 26. However, when fixation device 12 is intended to be placed near IMD 14 on cranium 24, fixation device 12 may be constructed out of one or more polymers or other non-electrically conductive materials in order to reduce or eliminate eddy currents that may cause heating of fixation device 12 during wireless charging of IMD 14. In some examples, fixation device 12 may be constructed with a biocompatible polymeric material such as silicone, polyurethane, nylon, polyether ether ketone (PEEK), polysulfone, polyethylene (e.g. ultra-high molecular weight polyethylene (UHMWPE)), or a combination thereof. Fixation device 12 may also have antibacterial features in some examples. Although fixation device 12 may be constructed of a unitary material, fixation device 12 may be constructed out of two or more materials in other examples. Materials and construction of fixation device 12 may be selected such that fixation device 12 is MRI compatible (e.g., fixation device 12 may be placed within the magnetic field and electrical fields of an MRI machine with substantially no damage to fixation device 12, IMD 14, or the MRI device, or side effects to patient 26).

Fixation device 12 may retain one or more IMDs 14 in some examples. For example, fixation device 12 may extend over two IMDs 14 where one IMD 14 is stacked on top of another IMD 14, or fixation device 12 may extend over two IMDs 14 that are disposed adjacent to one another. In another example, fixation device 12 may be configured to extend over multiple IMDs that are spaced a distance from one another. And, in other examples, multiple fixation devices 12 may be used to retain one or more IMDs 14. For example, three fixation devices 12 may extend over IMD 14 in varying directions, e.g., longitudinally, laterally, and diagonally. The additional fixation devices 12 may cover a greater surface area of IMD 14 to provide a greater coefficient of friction between fixation device 12 and IMD 14 as well as between IMD 14 and cranium 24. The additional fixation devices 12 may prevent IMD 14 from moving/slipping within cranium recess 17. In other examples, multiple fixation devices 12 may provide additional securing force for IMD 14.

Lead 20 may include a plurality of electrodes, and IMD 14 may be configured to deliver stimulation to the brain of patient 26 via the electrodes. A proximal end of lead 20 may be connected to adaptor 16 that electrically couples to a header of IMD 14. In some examples, IMD 14 may be coupled to two leads 20 that extend through a single burr hole 22 in cranium 24 or each lead 20 extend through a separate burr hole 22 in cranium 24 (e.g., to access separate hemispheres of the brain of patient 26). In some examples, lead 20 may include one or more electrodes that are implanted or otherwise placed adjacent to the target tissue. One or more electrodes may be disposed at a distal tip of lead 20 and/or at other positions at intermediate points along lead 20. Electrodes of lead 20 may deliver electrical stimulation (e.g., electrical signals generated by an electrical stimulation generator in IMD 14) to tissue of patient 26. The electrodes may be configured as electrode pads on a paddle lead, cylindrical (e.g., ring) electrodes surrounding the body of the lead, conformable electrodes, cuff electrodes, segmented electrodes (e.g., multiple electrodes located at the same axial location of the lead but different circumferential locations of the lead), or any other type of electrodes capable of forming unipolar, bipolar or multipolar electrode configurations for therapy. In general, ring electrodes may be arranged at different axial positions at the distal ends of lead 20.

Using such electrodes of lead 20, IMD 14 may deliver electrical stimulation energy (e.g., current or voltage-based pulses) to the one or more targeted locations within patient 26 according to one or more therapy/stimulation program. In some examples, IMD 14 may deliver stimulation to the brain of patient 26 to provide DBS therapy or to stimulate the cortex of the brain. IMD 14 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

Although lead 20 is described as generally delivering or transmitting electrical stimulation signals, lead 20 may additionally, or alternatively, transmit electrical signals from patient 26 to IMD 14 for sensing and monitoring functions of IMD 14. Alternatively, or additionally, lead 20 and IMD 14 may be configured to provide other types of therapy through the delivery of a therapeutic agent to the target tissue of patient 26. For example, IMD 14 may additionally, or alternatively, deliver a therapeutic agent such as a pharmaceutical, biological, or genetic agent (e.g., via a fluid delivered by a pump). In these examples, lead 20 may function as a catheter or IMD 14 may be otherwise coupled to a catheter. And fixation devices 12 may be used in any of the examples to retain IMD 14 as well as lead 20.

A user, such as a clinician or patient 26, may interact with a user interface of an external programming device 18 to program IMD 14. Programming of IMD 14 may refer generally to the generation and transfer of commands, programs, or other information to control the operation of IMD 14. For example, programming device 18 may transmit programs, parameter adjustments, program selections, group selections, or other information to control the operation of IMD 14, e.g., by wireless telemetry or wired connection. In some examples, programming device 18 may be primarily intended for use by a clinician, a patient, or both. In some examples, a user(s) may program and charge IMD 14 using one device or multiple programming devices 18.

IMD 14 is just one example of an IMD that can be placed in recess 17. An IMD may be constructed to have a different size and/or shape in other examples. As shown in the example of FIG. 1A, IMD 14 is generally rectangular in shape (e.g., a rectangular cuboid). IMD 14 can also be constructed to have other shapes, including other geometric shapes, e.g., square or cuboid, a triangle or pyramid, or a cylinder or sphere, or any other three-dimensional shape having one or more curved and/or flat surfaces.

Figure 1B:
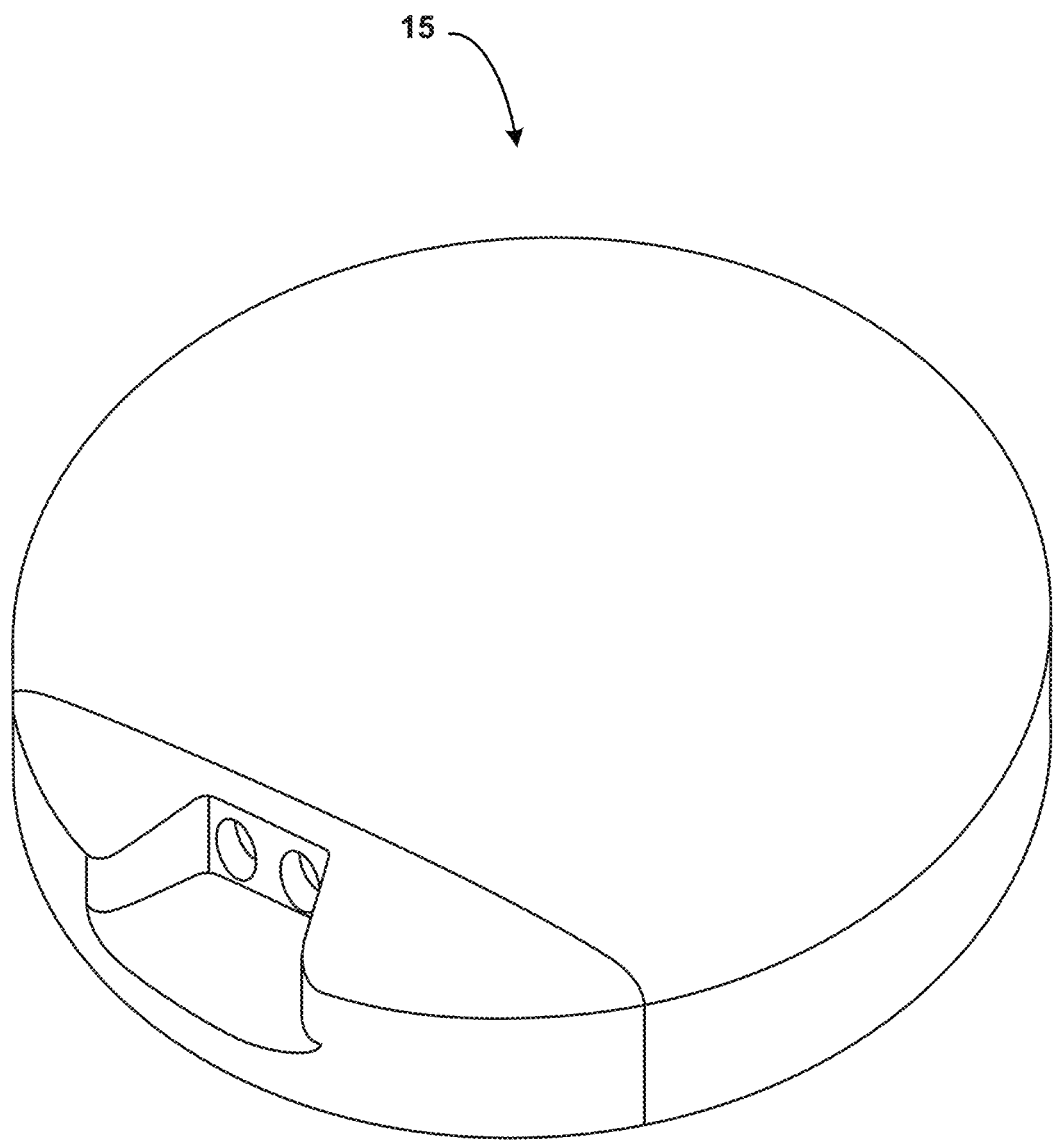
FIG. 1B is a perspective drawing illustrating another example medical device, in accordance with one or more aspects of this disclosure.

FIG. 1B is a perspective drawing illustrating another example IMD 15, e.g., an alternative of example medical device IMD 14, in accordance with one or more aspects of this disclosure. As shown in FIG. 1B, the shape of IMD 15 is generally cylindrical, with two relatively parallel flat circular surfaces joined by a curved surface around the perimeter of each circular surface. IMD 15 also has an inset portion configured to accept two medical leads, each lead similar to lead 20 of FIG. 1A. The size and shape of fixation device 12 (of FIG. 1A) may be configured to achieve the desired level of interference (or contact) with IMDs, e.g., IMDs 14 and 15. In some examples, the desired level of interference between fixation device 12, IMDs 14 and 15, and recess 17 may be selected to achieve a desired level of fixation force applied by fixation device 12 to the respective IMD 14 or 15. Based on, at least in part, user preferences and/or expected lifestyle requirements, the desired fixation force may vary from patient to patient.

The material (flexibility) of fixation device 12 can be selected to achieve a desired fixation force against the housing of IMDs 14 and 15. A clinician may increase the force by stretching fixation device 12 further over the housing of IMDs 14 and 15. In some examples, if fixation device 12 extends for a short distance compared to the size of IMDs 14 and 15 and recess 17, fixation device 12 may need to flex over IMDs 14 and 15. Thereby, fixation device 12 may apply a greater fixation force by stretching further over the housing of IMDs 14 and 15 when compared to a relatively longer fixation device 12 made of the same or substantially similar material, that may not need to flex over IMDs 14 and 15 in order to secure IMDs 14 and 15 within recess 17. The length of fixation device 12 can be determined, at least in part, based on the desired level of fixation force of fixation device 12. In other examples, a material may be selected that has a greater elastic modulus to construct fixation device 12 with less flexibility that can provide greater force against IMD 15 than a more flexible material.

In some examples, fixation device 12 may be sized, e.g., a length and/or a width of fixation device 12, to span a variety of shapes and sizes for the recess 17 and IMDs 14 and 15. For example, the length of fixation device 12 may extend a distance greater than 4 inches, greater than 2 inches, less than 4 inches, less than 2 inches, from about 0.5 inches to 2 about inches, from about 2 inches to about 5 inches, from about 2 inches to about 3 inches, from about 2 inches to about 4 inches, from about 1 inch to about 3 inches, or from about 1 inch to about 2 inches. The ranges listed for the length of fixation device 12 are examples, but fixation device 12 may have other lengths in other examples. In some examples, one, two, or more fixation devices 12 may be used to secure IMD 15 in crossing configurations, side-by-side configurations, or any other spatial relationship between the multiple fixation devices 12.

Figure 2A:
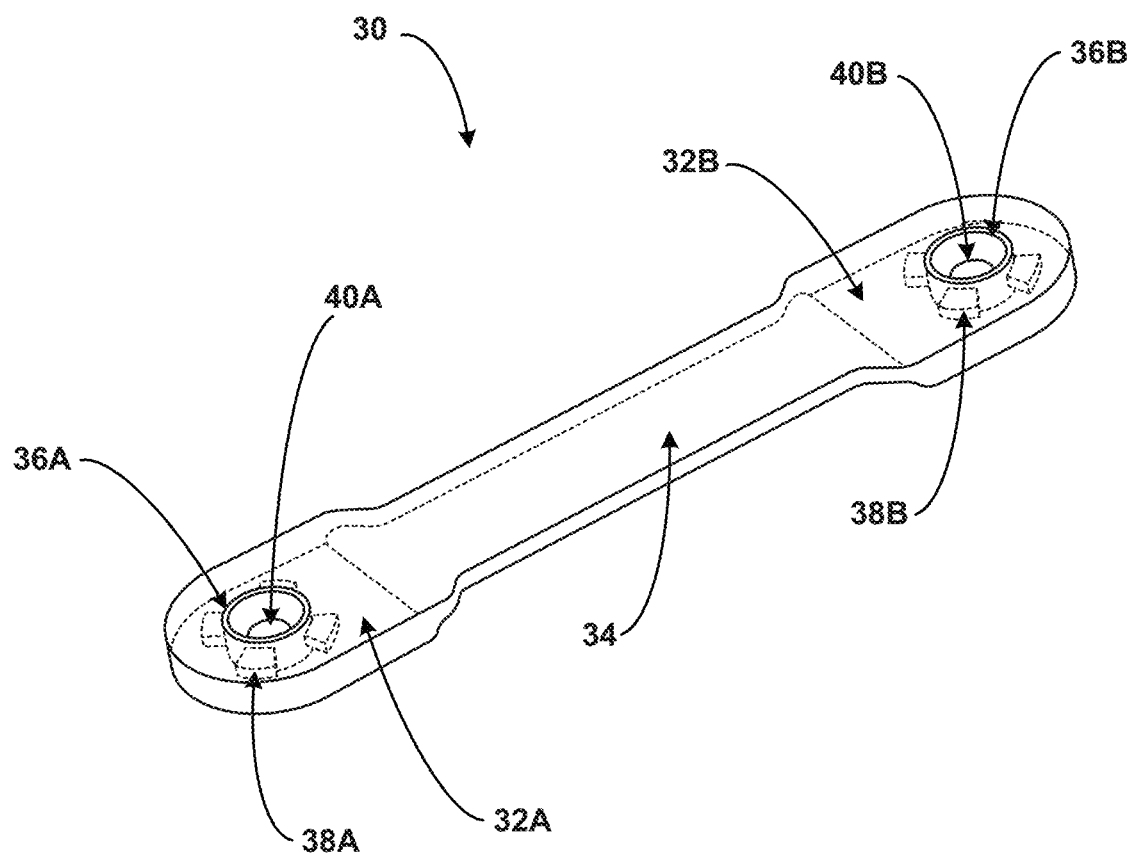
FIG. 2A is a perspective view of an example fixation device configured to secure a medical device to a cranium, in accordance with one or more aspects of this disclosure.

FIG. 2A is a conceptual diagram illustrating an example fixation device 30, in accordance with one or more aspects of this disclosure. Fixation device 30 may be similar to fixation device 12, e.g., having the same material, general shape, and/or features. In the example of FIG. 2A, fixation device 30 includes a first base portion 32A, a second base portion 32B, a connecting strap 34, a first insert 36A, a second insert 36B, a first tabs 38A, and a second tabs 38B. First base portion 32A defines a first inner channel 40A, and second base portion 32B defines a second inner channel 40B. Connecting strap 34 extends between and connects first base portion 32A to second base portion 32B. In some examples, first base portion 32A, second base portion 32B, and connecting strap 34 may be part of the flexible band of fixation device 30.

Fixation device 12 may be constructed of a single material, but fixation device 12 may be constructed of two or more materials in other examples. For example, first base portion 32A and second base portion 32B may be constructed of a material that is more rigid (e.g., higher elastic modulus) than connecting strap 34. First base portion 32A and second base portion 32B may be constructed of a more rigid material that the material of connecting strap 34 to retain first insert 36A and second insert 36B within their respective base portions. Conversely, connecting strap 34 may be constructed of a more flexible material (e.g., lower elastic modulus) than the material of first and second base portions 32A and 32B in order to bend and/or stretch over medical devices of varying sizes and shapes.

Fixation device 30, including first base portion 32A, second base portion 32B, and connecting strap 34, may be formed into various shapes and sizes to accommodate requirements for different implantable devices and/or different patients. For example, fixation device 30 may be constructed in a shape with a small or minimized height (e.g., thickness of connecting strap 34 and first and second base portions 32A and 32B to reduce bulk of the device that would extend away from IMD 14 and the exterior surface of cranium 24. Since fixation device 30 may raise the scalp of patient 26 after implantation, constructing fixation device 30 with a small height may reduce the distance that the scalp extends away from cranium 24. Connecting strap 34 may be constructed of a continuous and solid material. However, in other examples, connecting strap 34 may be constructed to define one or more holes, voids, gaps, slots, slits, cut-outs, and/or any other structural feature that promotes flexibility and/or elasticity. For example, connecting strap 34 may define several slots that decreases the stiffness of connecting strap 34. Put another way, connecting strap 34 may define and/or contain one or more structures that enables connecting strap 34 to deform or stretch over IMD 14.

Fixation device 30 may be described as defining a top side, bottom side, and two side walls. In some examples, first base portion 32A, second base portion 32B, and connecting strap 34 may form substantially planar surfaces across the top side, bottom side, and two side walls. In other examples, as shown in FIG. 2A, the transition of the bottom side and two side walls from both of first base portion 32A and second base portion 32B to connecting strap 34 ramps or steps inward such that the bottom side and two side walls of connecting strap 34 define a cross-sectional dimension of connecting strap 34 that is smaller than the cross-sectional dimension of first base portion 32A and second base portion 32B. In this manner, connecting strap 34 may define a smaller width and height than that of first base portion 32A and second base portion 32B. In other examples, the cross-sectional area of connecting strap 34 may be smaller than the cross-sectional area of first base portion 32A and second base portion 32B by changing the plane of only one of the top side, the bottom side, a first side wall or a second side wall of connecting strap 34. For example, the bottom surface of connecting strap 34 may lie on a plane closer to the midline of fixation device 30 than the bottom surface of first base portion 32A and second base portion 32B. In other words, one or more dimensions of connecting strap 34 may be reduced when compared to first base portion 32A and second base portion 32B to arrive at a smaller cross-sectional area for connecting strap 34. As an example, a single side wall of connecting strap 34 may be closer to the midline or center axis of fixation device 12 than the side walls of first base portion 32A and second base portion 32B such that connecting strap 34 has a reduced cross-sectional dimension when compared to first base portion 32A and second base portion 32B. In another example, the top side of connecting strap 34 may be closer to the midline or center axis of fixation device 30 such that connecting strap 34 has a reduced cross-sectional dimension when compared to first base portion 32A and second base portion 32B. The transitions from the surfaces of first base portion 32A and second base portion 32B to connecting strap 34 may include one or more steps and/or one or more ramps.

Connecting strap 34 may be constructed with a strap thickness in the range from approximately 0.5 millimeters (mm) (20 thousandths of an inch (thou)) to approximately 1.5 mm (60 thou). However, connecting strap 34 may be thinner or thicker in other examples. First base portion 32A and second base portion 32B may each have a thickness and width that are both greater than the thickness and width of connecting strap 34. However, in other examples, connecting strap 34 may have a width and/or thickness greater than that of first base portion 32A and second base portion 32B.

In some examples, first base portion 32A may be substantially similar in material and/or dimension as second base portion 32B. In other examples, first base portion 32A and second base portion 32B may be different from each other (e.g., a different shape, size, and/or material). For example, first base portion 32A may be triangular-shaped and constructed of a more rigid material and of a smaller size than second base portion 32B. Second base portion 32B may rectangular-shaped and constructed of a more flexible material and of a larger size than first base portion 32A. Similarly, first insert 36A and second insert 36B may be the same or may be different from each other in one or more characteristics such as shape, size, or material.

First insert 36A and second insert 36B (collectively "inserts 36") may be configured to be disposed within respective first base portion 32A and second base portion 32B. Inserts 36 may each define respective inner channels 40A and 40B in order for each of inserts 36 to receive a respective attachment mechanism (e.g., a bone screw, nail, etc.). Inserts 36 may be constructed of a material more rigid (e.g., higher elastic modulus) than the material of first base portion 32A and second base portion 32B. For example, inserts 36 may be constructed of a rigid molded plastic or other polymer. Example materials for inserts 36 may include PEEK, nylon, polysulfone, polyethylene (e.g. ultra-high molecular weight polyethylene (UHMWPE)), high density polyurethane, polyoxymethylene, polyethylene terephthalate (PETE), or any other biocompatible material. Each of inserts 36 include one or more tabs 38A and 38B. Each of the tabs 38A and 38B may extend radially outward from an outer surface of the respective insert 36. Tabs 38A and 38B may be formed into any shape of any size appropriate for inserts 36 and fixation device 30. In this manner, tabs 38A and 38B may be configured to secure the respective insert 36 within respective first base portion 32A and second base portion 32B.

Figure 2B:
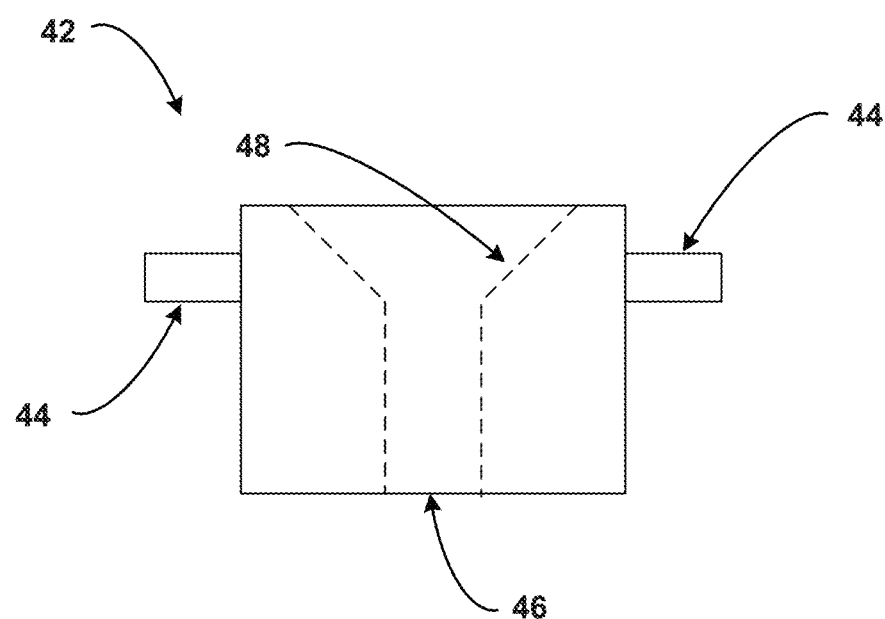
FIG. 2B is a side view of an example insert for a fixation device, in accordance with one or more aspects of this disclosure.

FIG. 2B is a side view of an example insert 42 for a fixation device, in accordance with one or more aspects of this disclosure. Insert 42 may be similar to first insert 36A and second insert 36B of FIG. 2A. In the example of FIG. 2B, insert 42 includes one or more tabs 44 and defines an inner channel 46 and a recess 48. There may be a plurality of tabs 44 extending from the outer surface of insert 42. In some examples, a plurality of tabs 44 provide a retaining force against the surrounding material of the base portion of the flexible band to secure insert 42 within its respective fixation device, e.g., fixation device 12. More or less tabs 44 may be used to secure insert 42 to cranium 24 depending on the intended use of the fixation device.

In some examples, as shown in FIG. 2B, inner channel 46 includes recess 48. Recess 48 may have a variety of configurations including a smooth surface disposed at any angle to inner channel 46. In some examples, recess 48 may be a conical recess that opens from inner channel 46. Inner channel 46 and recess 48 may together be configured to receive a bone screw or other attachment mechanism. The angle of recess 48 may be similar to the angle of a flat-head bone screw such that the outer surface of the bone screw remains flush with or below an outer surface of insert 42. By keeping an outer surface of the bone screw flush with outer surface of insert 42, the bone screw may provide a relatively smooth surface under the scalp to avoid becoming snagged with objects, injuring the patient, or damaging other medical devices. In addition, the size and shape of insert 42 may be varied in order to create a secure fit with a fixation device. In one example, recess 48 may be a recessed flat-bottomed hole that may be used with a socket-head capscrew.

Figure 3:
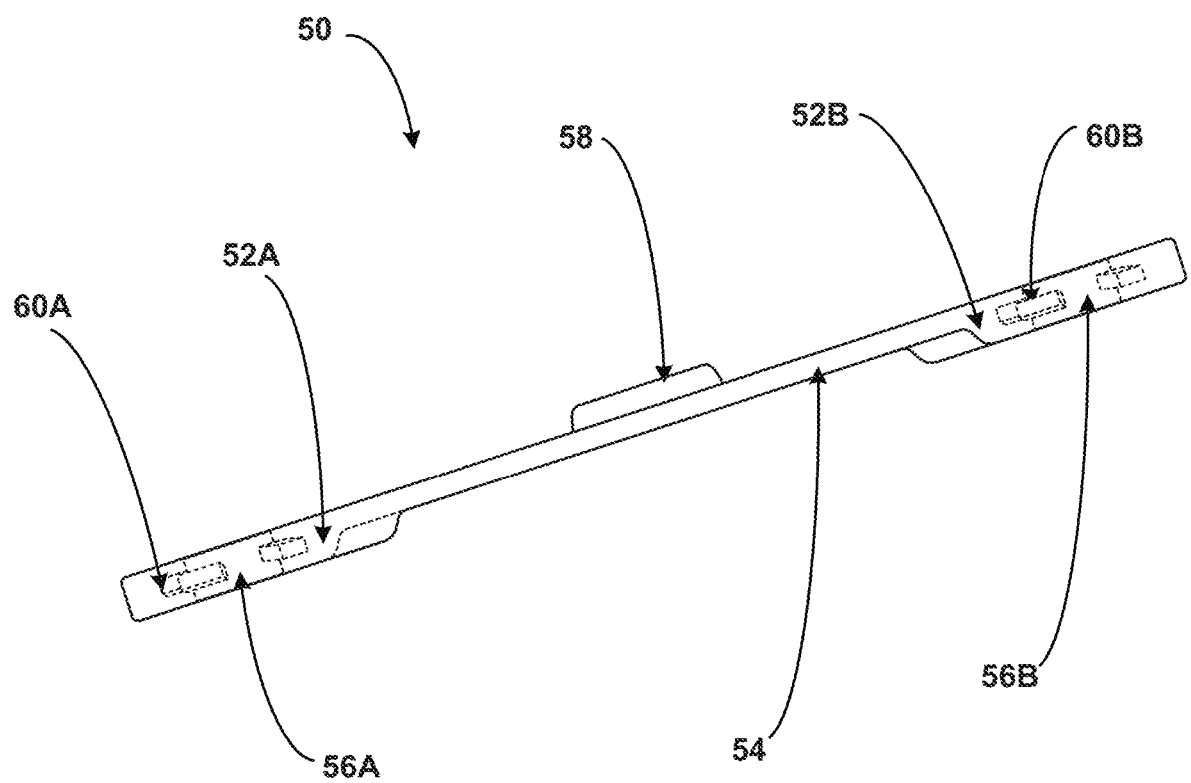
FIG. 3 is a side view of an example fixation device configured to secure a medical device to a cranium, in accordance with one or more aspects of this disclosure.

FIG. 3 is a side view of an example fixation device 50 configured to secure a medical device (e.g., IMD 14) to cranium 26, in accordance with one or more aspects of this disclosure. Fixation device 50 may be similar to fixation devices 12 and 30, including being constructed out of similar materials. In the example of FIG. 3, fixation device 50 includes a first base portion 52A, a second base portion 52B, a connecting strap 54, a first insert 56A, a second insert 56B, a standoff structure 58, first tabs 60A, and second tabs 60B. The flexible band of fixation device 50 may include first base portion 52A, second base portion 52B, and connecting strap 54.

Standoff structure 58 may be formed on or attached to any part of connecting strap 54. Standoff structure 58 may be configured to contact a medical device, such as IMD 14, and increase a fixation force between the flexible band and IMD 14 by creating more interference between fixation device 50 and IMD 14. Standoff structure 58 may be disposed on a single side of fixation device 50 to enable fixation device 50 to be flipped based on whether or not the clinician desires the additional force by placing standoff structure 58 against IMD 14. For example, if IMD 14 does not extend out from recess 17 far enough to be subject to retaining force from fixation device 50, a clinician may place standoff structure 58 against IMD 14 to provide the desired retaining force against IMD 14. In some examples, fixation device 50 may include multiple standoff structures 58 disposed on a single side of fixation device 50 in order to increase the fixation force. In some examples, standoff structures 58 disposed on both sides connecting strap 54 may have differing heights from connecting strap 54 to allow for different forces based on which side of connecting strap 54 is placed against IMD 14. The size and shape of standoff structure 58 may also be configured to achieve the desired level of interference. Standoff structure 58 may be any shape or geometry, including, but not limited to circular, oval, rectangular, triangular, polygonal shapes or any combinations thereof. Standoff structure 58 may have any type of surface such as a surface that is smooth, studded, dimpled, wave-like, or any combinations thereof. In some examples, standoff structure 58 and fixation device 50 are constructed of the same material. In other examples, standoff structure 58 may be constructed of a material different than the material of the flexible band of fixation device 50.

Figure 4A:
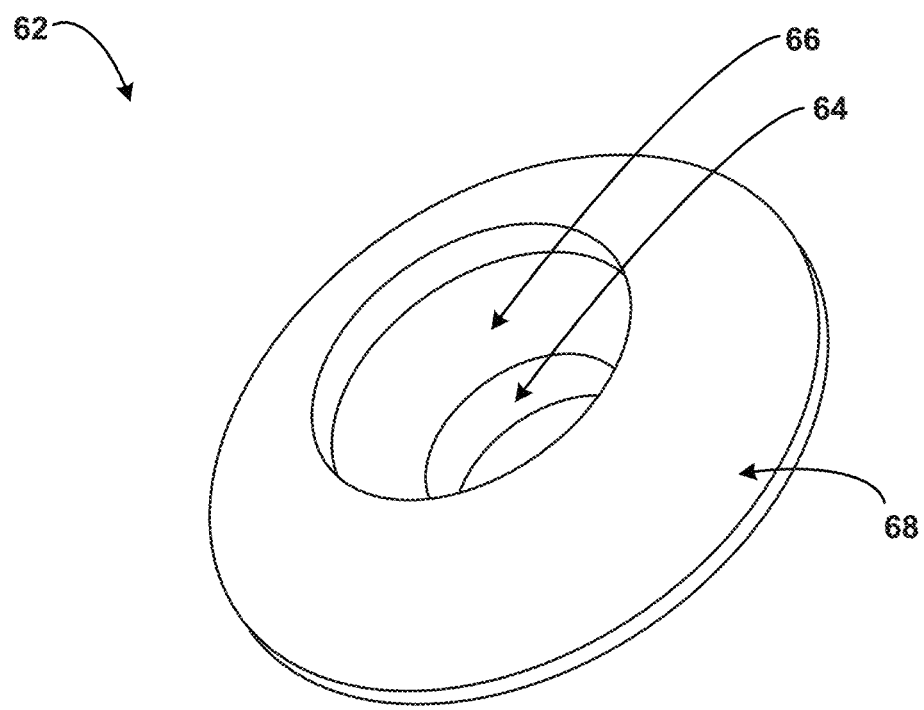
FIG. 4A is a top perspective view of an example suture button, in accordance with one or more aspects of this disclosure.

FIG. 4A is a top perspective view of an example suture button 62, in accordance with one or more aspects of this disclosure. Suture buttons, such as suture button 62, may be attached to cranium 24 and receive suture or other similar structure that is disposed over IMD 14 to secure IMD 14 within recess 17. In the example of FIG. 4A, suture button 62 defines an inner channel 64 and an outer surface 68. In some examples, inner channel 64 includes a recess 66, which may be conical in shape in some examples. Inner channel 64 may be similar to inner channels 40A, 40B, and 56 of fixation devices 12 and 30. An attachment mechanism, such as a bone screw, may extend through inner channel 64 to secure suture button 62 to cranium 24. Recess 66 provides space for a bone screw to be fully inserted in suture button 62 and remain flush with or below the outer surface 68 of suture button 62. Outer surface 68 of suture button is shown as being rounded or convex-shaped, but outer surface 68 may have other shapes in other examples. As shown in greater detail in FIGS. 4C and 4D, outer surface 68 may be any geometrical shape to retain a suture including concave, convex, wave-like shape, flat, a series of bumps, cutouts, and indentations, or any combination thereof. In contrast to fixation device 12, where connecting strap 34 is used to retain IMD 14, suture button 62 may retain IMD 14 with a suture, wherein an underside of suture button 62 (not shown in FIG. 4A) is configured to receive the suture. Suture button 62 may be constructed of the same materials as fixation devices 12, 30, and 50 as described above.

Figure 4B:
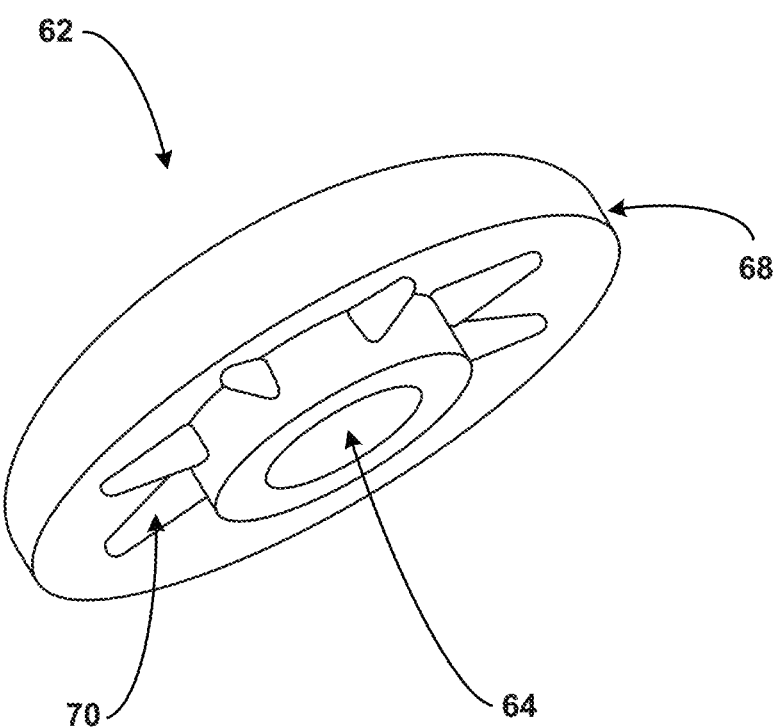
FIG. 4B is a bottom perspective view of an example suture button, in accordance with one or more aspects of this disclosure.

FIG. 4B is a bottom perspective view of an example suture button 62, in accordance with one or more aspects of this disclosure. In the example of FIG. 4B, suture button 62 defines inner channel 64 and includes outer surface 68 and suture fixation barbs 70. Suture fixation barbs 70 are disposed on the underside, or bottom, of suture button 62 to provide friction for sutures that are wrapped around the suture button 62. For example, if a suture is wrapped around the base of suture button 62, portions of the suture will contact fixation barbs 70 to prevent the suture from moving (e.g., slipping) with respect to suture button 62. Suture fixation barbs 70 may have varying shapes and sizes configured to increase frictional force with sutures wrapped around suture button 62. In some examples, suture fixation barbs 70 may also be configured to contact cranium 24 to prevent suture button 62 from rotating when sutures are pulled around suture button 62 on cranium 24. In the example of FIG. 4B, suture fixation barbs 70 are shown on the bottom, or underside, of suture button 62 that is configured to face the exterior surface of cranium 24. In other examples, suture fixation barbs 70 may be disposed on other parts of suture button 62 that are configured to accept sutures. For example, suture fixation barbs 70 may be disposed in a middle portion of outer surface 68 where the middle portion is configured to retain sutures. Suture button 62 may use more than one means to retain a suture. For example, suture button 62 may use a combination of suture fixation barbs 70 and outer surface 68 to retain a plurality of sutures. In some examples, the different structures may be located at different locations on the suture button 62. By suture button 62 having multiple different structures to retain a suture, a clinician may decide which structure or combinations of structures provides effective securement for the suture depending on the implantation circumstances such as size and shape of IMD 14 and/or curvature or cranium 24.

Suture buttons 62 may be used in a variety of configurations on cranium 24. Depending on several characteristics, including the size and shape of IMD 14, cranium 24, and cranium recess 17, a plurality of suture buttons 62 may be used to retain IMD 14 on cranium 24. In one example, two suture buttons 62 may be disposed on opposing sides of recess 17 such that sutures can cross over IMD 14 and attached to the respective suture buttons. For a plurality of suture buttons 62, each suture button 62 may be the same or different, e.g., different material, outer surface 68 features, and presence, or lack thereof, of suture fixation barbs 70. A webbing of suture material (e.g., multiple portions of suture crossing over IMD 14) may extend between the plurality of suture buttons 62 in other examples. The suture-created webbing may apply additional fixation force to retain IMD 14 on cranium 24 and/or reduce the risk of IMD 14 moving or rotating within recess 17. In some examples, a material other than a suture may be used to extend between the suture buttons 62, such as a different fabric, metal wire, extruded polymer, or the like.

Figure 4C:
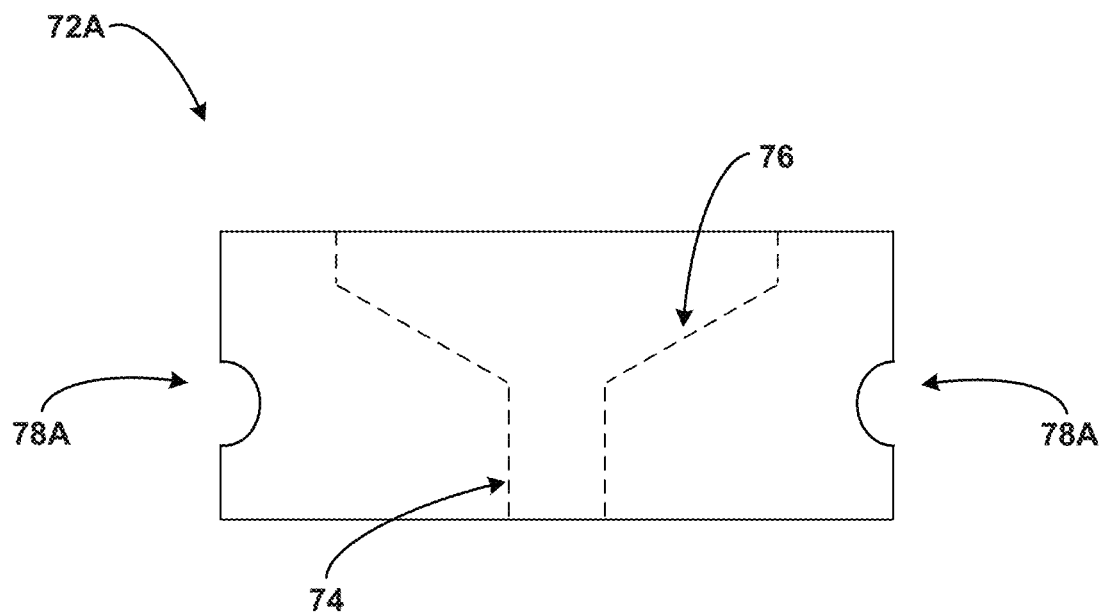
FIGS. 4C and 4D are side views of example suture buttons, in accordance with one or more aspects of this disclosure.
Figure 4D:
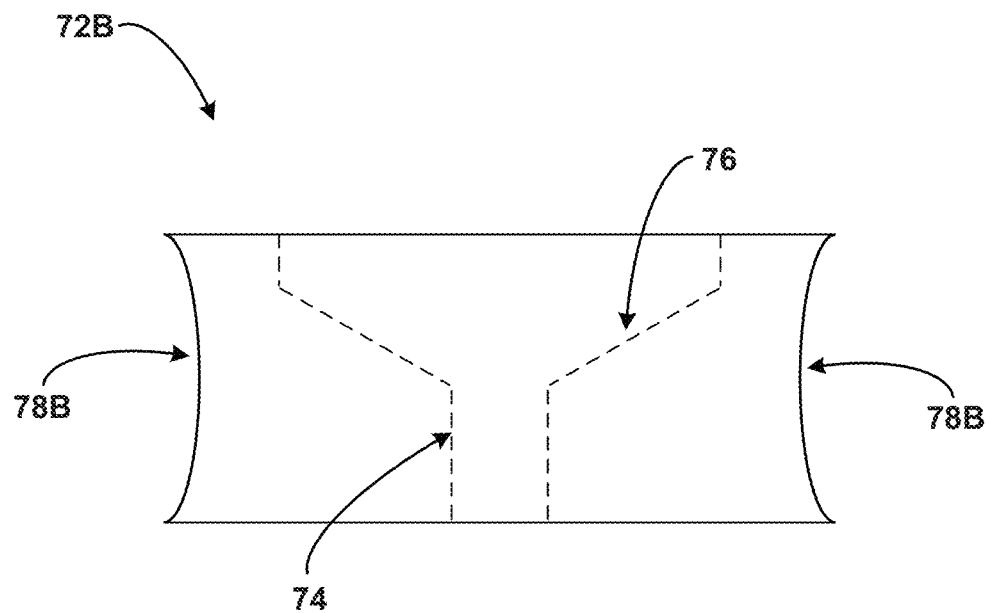

FIG. 4C is a side view of an example suture button 72A, in accordance with one or more aspects of this disclosure. Suture button 72A may be similar to suture button 62. For example, suture buttons 62 and 72A may be constructed of similar materials or have similar sizes. In the example of FIG. 4C, suture button 72A defines an inner channel 74, a recess 76, and an outer surface 78A. Outer surface 78A may be shaped and sized to receive suture around the exterior of suture button 62 such that the suture can retain a medical device. As described above, outer surface 78A may for formed into a variety of different shapes and sizes. As shown in FIG. 4C, a semi-circular recess is formed into outer surface 78A, wherein suture can be disposed within the recess. In another example, two semi-circular protrusions may extend around the circumference and outwards from outer surface 78A in order to retain a suture between the two semi-circular protrusions. In some examples, suture fixation barbs 70 may be used in addition to outer surface 78A to retain a suture. FIG. 4D, as described below, displays another example of an outer surface of a suture button.

FIG. 4D is a side view of an example suture button 72B, in accordance with one or more aspects of this disclosure. In the example of FIG. 4D, suture button 72B defines an inner channel 74 and a recess 76 and includes an outer surface 78B. Outer surface 78B is concave-shaped in the example of FIG. 4D. The concave-shaped outer surface 78B may be configured to receive suture within the smaller circumferential portion of the concave shape such that the suture cannot slide off of suture button 72B. In other examples, outer surface 78B may be convex-shaped. Suture button 72B may be similar to suture buttons 62 and 72A. Like suture button 72A, suture fixation barbs 70 may be added to suture button 72B. For example, suture fixation barbs 70 may be added to a middle portion of outer surface 78B.

Figure 5A:
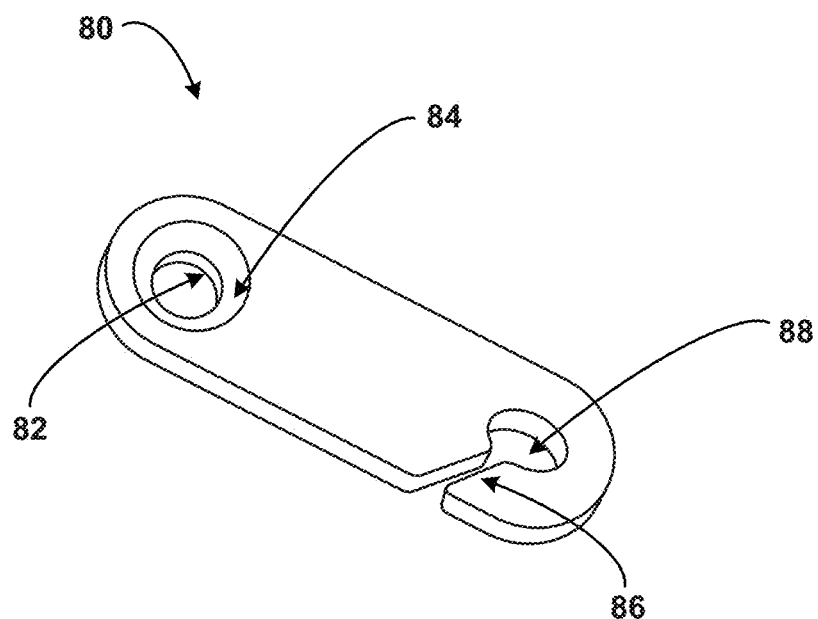
FIG. 5A is a perspective view of an example suture tab, in accordance with one or more aspects of this disclosure.

FIG. 5A is a perspective view of an example suture tab 80, in accordance with one or more aspects of this disclosure. In the example of FIG. 5A, suture tab 80 defines an inner channel 82, a recess 84, a suture tab slot 86, and a groove 88. Inner channel 82 may be similar to inner channels 40A, 40B, 46, 64, and 74. Similar to FIGS. 4A and 4B, an attachment mechanism, such as a bone screw, may extend through inner channel 82 to secure suture tab 80 to cranium 24. Recess 84 has an inner circumferential wall that may be conical shaped, for example, to provide space for a bone screw to be fully inserted in suture tab 80 so that the bone screw may be flush with suture tab 80. After suture tab 80 is attached to cranium 24, a clinician may slide suture through tab slot 86 and into groove 88 so that the suture may remain within groove 88. In other examples, tab slot 86 may not be necessary. In other examples, a loop of suture may be passed through tab slot 86 and into groove 88. Then, the clinician may tension the loop of suture and then secure suture tab 80 onto the cranium 24 with a bone screw.

In some examples, a system may use two or more suture tabs 80 to secure a medical device to a cranium. In addition, some suture tabs 80 may use more than one suture tab slot 86 and groove 88 to retain a suture. Each suture tab 80 may include two or more suture tab slots 86 and grooves 88 in order to create a webbing of sutures between suture tabs 80 to keep a medical device retained to cranium 24 or other body part of patient 26.

In some examples, suture tab 80 may be constructed of the same materials as fixation devices 12, 30, and 50 and suture button 62 as described above. For example, suture tab 80 may be constructed of a single material or more than one materials. Suture tab 80 may be constructed of three materials: a first material at inner channel 82, a second material by suture tab slots 86, and a third material disposed between the first and second material. The third material may be relatively more flexible in order to enable suture tab 80 to bend and fit the curvature of the cranium (e.g., such that suture tab 80 is non-planar). And the first and second material may be constructed of a more rigid material to provide a secure attachment point for sutures and attachment mechanisms, e.g., bone screws.

Suture tab 80 may be formed into varying shapes and sizes. For example, instead of a rectangular shape, suture tab 80 may be triangular. Suture tab slot 86 and groove 88 may have varying shapes and sizes as well. For example, suture tab slot 86 may be zig-zagged shaped to retain suture in groove 88. In some examples, inner channel 82 may have various geometries including flat, threaded, or ribbed. Inner channel 82 may be respectively threaded for a bone screw in order to increase attachment between suture tab 80 and the bone screw, or other attachment mechanism. In other examples, suture tab 80 may be ribbed in order to provide a friction fit between suture tab 80 and the attachment mechanism.

Figure 5B:
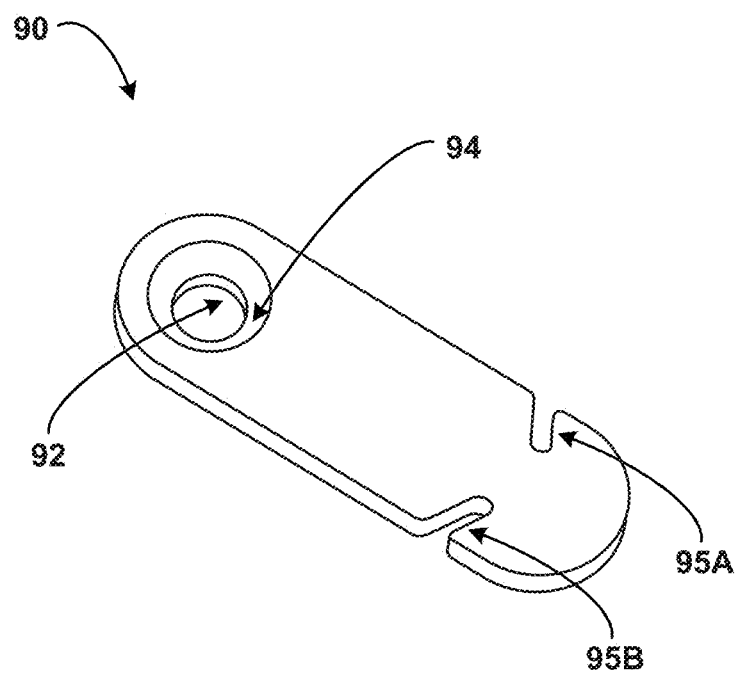
FIG. 5B is a perspective view of an example suture tab, in accordance with one or more aspects of this disclosure.

FIG. 5B is a perspective view of an example suture tab 90, in accordance with one or more aspects of this disclosure. In the example of FIG. 5B, suture tab 90 includes an inner channel 92, a recess 94, and suture tab slots 95. Suture tab 90 may be similar to suture tab 80. For example, suture tabs 80 and 90 may be constructed of similar materials. FIG. 5B shows one alternative to suture tab 80 of FIG. 5A for retaining sutures. Instead of one suture tab slot 86 with groove 88, as shown in FIG. 5A, two suture tab slots 95A and 95B together retain a single suture or respective sutures. Tab slots 95A and 95B may be angled forward such that tension in the opposite direction keeps sutures within tab slots 95A and 95B. In some examples, suture tab 90 may have more than two suture tab slots 95 to retain sutures.

Figure 5C:
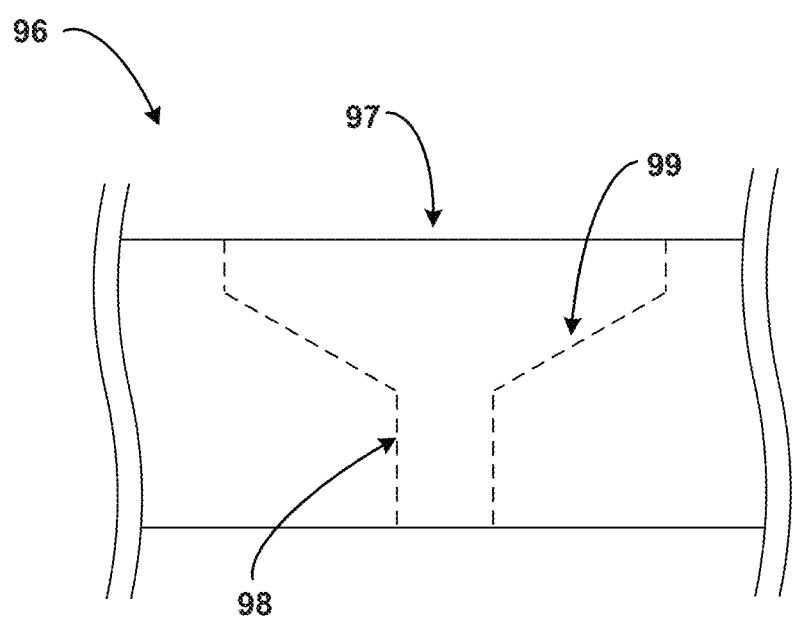
FIG. 5C is a side view of an example suture tab portion, in accordance with one or more aspects of this disclosure.

FIG. 5C is a side view of an example suture tab portion 96, in accordance with one or more aspects of this disclosure. Suture tab portion 96 may be an alternative portion of suture tab 90 that defines inner channel 92. In the example of FIG. 5C, suture tab portion 96 defines inner channel 98 and recess 99. As shown, recess 99 is a conically shaped recess configured to accept a head of a bone screw. Inner channel 97 may be similar to inner channels 40A, 40B, 46, 64, 74, 82, and 92. And suture tab portion 96 may be similar to insert 42 and suture buttons 72A and 72B in terms of function, and in some cases, in terms of shape. For example, suture tab portion 96 may be constructed of the same material as insert 42 and may be the same size as suture buttons 72A and 72B.

Figure 6A:
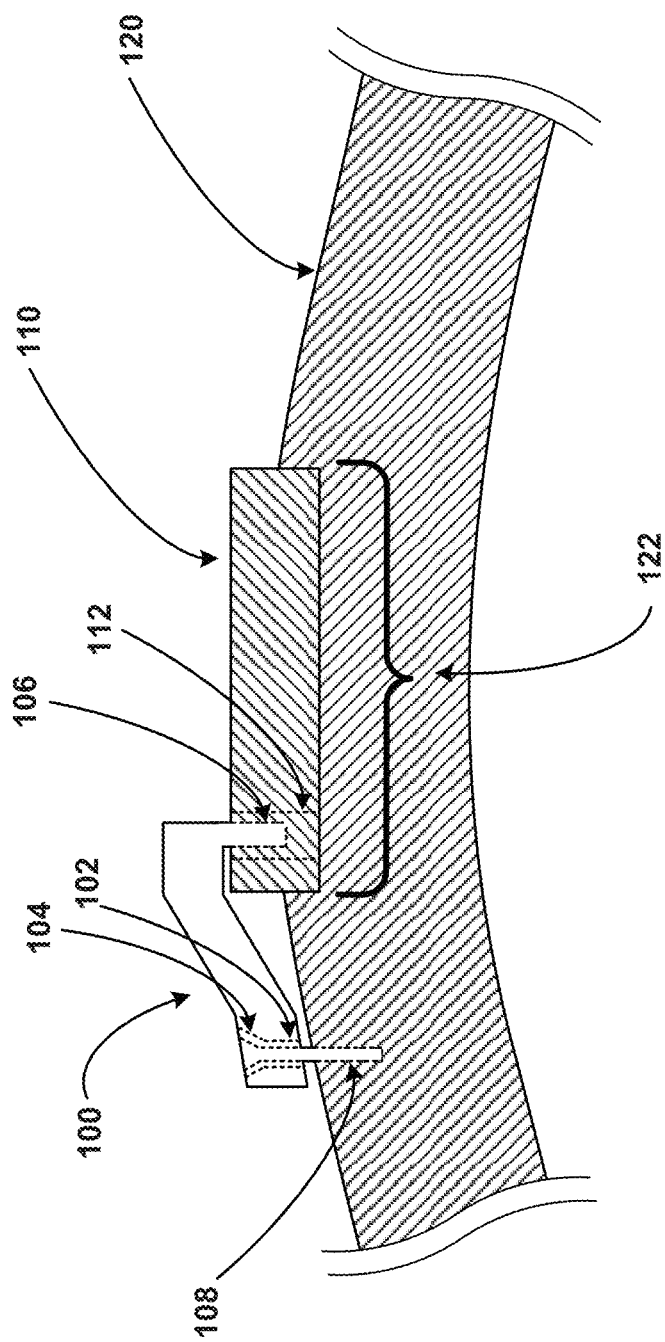
FIG. 6A is a conceptual diagram illustrating an example medical system including a bent fixation tab, in accordance with one or more aspects of this disclosure.

FIG. 6A is a conceptual diagram illustrating a system including an example bent fixation tab 100. The example of FIG. 6A also includes a bone screw 108 and IMD 110 defining inner channel 112. Bent fixation tab 100 defines inner channel 102 and recess 104 and includes prong 106. Inner channels 102 and 112 may be similar to inner channels 40A, 40B, 46, 64, 74, 82, 92, and 97. Bone screw 108 is used as the attachment mechanism to be inserted through inner channel 102 and secure bent fixation tab 100 to a cranium 120. Prong 106 of bent fixation tab 100 may be inserted through inner channel 112 of IMD 110. With prong 106 inserted in inner channel 112 and bone screw 108 inserted through inner channel 102, bent fixation tab 100 may secure IMD 110 into cranium recess 122. Cranium recess 122 may reduce the amount IMD 110 extends above cranium 120. In some examples, cranium recess 122 may prevent IMD 110 from becoming damaged or dislodged from cranium 120 because less IMD 110 may not extend as far above curved surface of cranium 120. In some examples, cranium recess 122 may not be present, and IMD 110 may be secured to cranium 120.

Bent fixation tab 100 may be similar to fixation device 12. For example, bent fixation tab 100 and fixation device 12 may be constructed out of similar materials. However, bent fixation tab 100 may be formed of a generally rigid material that applied a force against IMD 110. Outer surface of bent fixation tab 100 may be formed into various shapes and sizes. In some examples, the outer surface of bent fixation tab 100 may be curved to approximate the curvature of cranium 120. In the example of FIG. 6A, only one attachment mechanism, bone screw 108, was used to secure IMD 110 to cranium 120. In other examples, there may be multiple attachment mechanisms, such as bone screw 108, and corresponding inner channels 102 to secure IMD 110 to cranium 120. For example, bent fixation tab 100 may have multiple inner channels 102 and recesses 104 to accommodate multiple bone screws 108 to increase the fixation force of bent fixation tab 100 to cranium 120. If additional fixation force is desired depending on the circumstances of patient 26, additional attachment mechanisms may be used to help secure bent fixation tab 100 to cranium 120. Similarly, bent fixation tab 100 may have multiple prongs 106 and corresponding multiple inner channels 112 to ensure IMD 110 remains secure in cranium recess 122 or to cranium 120.

In the example of FIG. 6A, bent fixation tab 100 is shown as being disposed on a single side of IMD 110 and covering a portion of IMD 110. In some examples, bent fixation tab 100 may be disposed on multiple sides of IMD 110 and extend varying amounts over IMD 110. In one example, bent fixation tab 100 may be disposed to substantially cover IMD 110 and attach to cranium 120 on multiple sides with multiple bone screws 108.

Figure 6B:
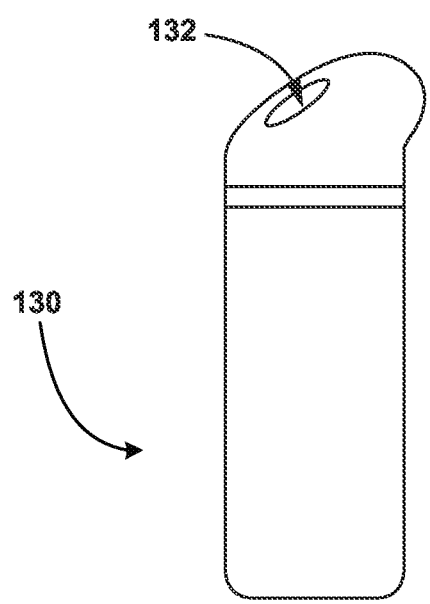
FIG. 6B is a conceptual diagram illustrating an example medical device, in accordance with one or more aspects of this disclosure.

FIG. 6B is conceptual diagram illustrating an example IMD 130, in accordance with one or more aspects of this disclosure. In the example of FIG. 6B, IMD 130 is shown defining an inner channel 132. Inner channel 132 may be formed into various shapes and sizes to receive bent fixation tab 100 or an attachment mechanism, such as a bone screw, prong, or staple. In some examples, multiple inner channels 132 may be disposed on IMD 130. IMD 130 may be similar to IMD 14 and IMD 110. For example, IMD 130 may be constructed of similar materials as IMD 14.

Figure 6C:
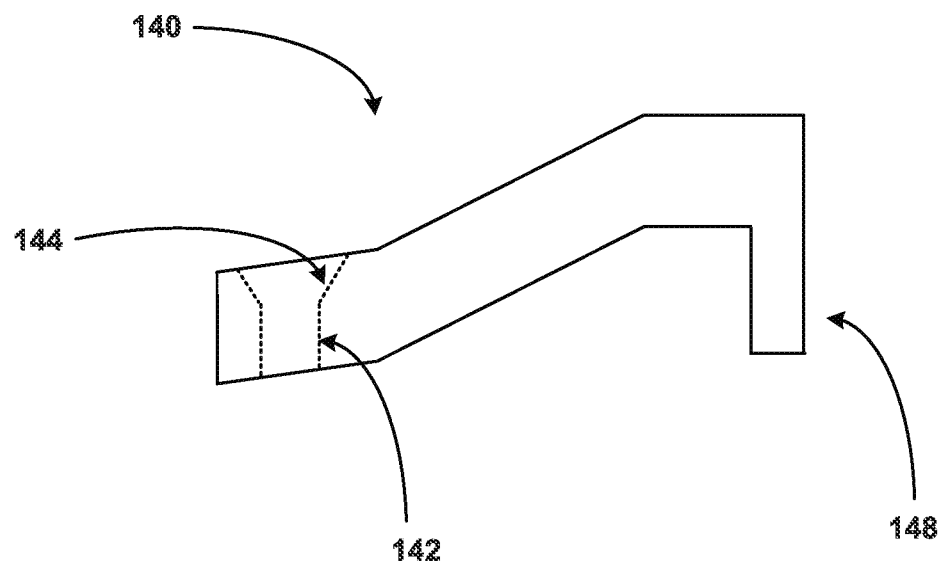
FIGS. 6C and 6D are side and top views of an example bent fixation tab, in accordance with one or more aspects of this disclosure.
Figure 6D:
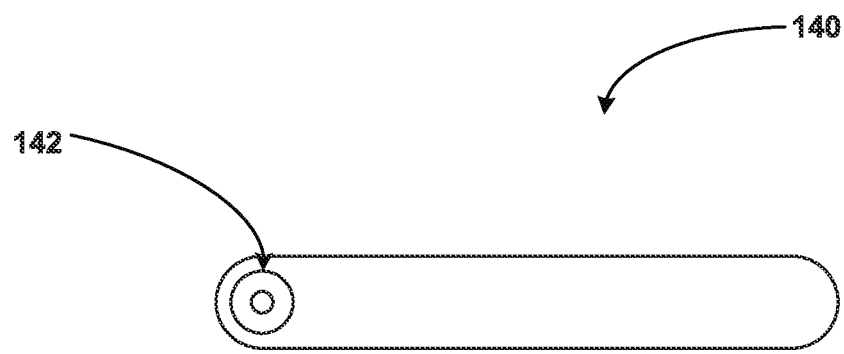

FIGS. 6C and 6D are side and top views, respectively, of an example bent fixation tab 140, respectively, in accordance with one or more aspects of this disclosure. In some examples, bent fixation tab 140 may be similar to bent fixation tab 100 of FIG. 6A. Bent fixation tab 140 defines an inner channel 142 and a recess 144 and includes a prong 148. Prong 148 may be configured to be inserted into a recess of an IMD. An attachment mechanism (e.g., a bone screw) may be inserted through inner channel 142 to secure bent fixation tab 140 to a cranium as well as connect bent fixation tab 140 to a medical device. Both a bottom side and a top side of bent fixation tab 140 may be shaped and sized to be flush with a cranium. In the example of FIG. 6C, bent fixation tab 140 is shown extending upwards but bent fixation tab 140 may have other shapes. For example, bent fixation tab 140 may be approximately straight between the two ends of bent fixation tab 140. In some examples, bent fixation tab 140 may have multiple inner channels 142 and/or multiple prongs 148. Bent fixation tab 140 may be constructed of rigid materials that generally do not substantially deform when implanted within a patient. For example, bent fixation tab 140 may be formed of a rigid polymer such as PEEK, nylon, polysulfone, polyurethane, polyethylene (e.g. ultrahigh molecular weight polyethylene (UHMWPE)), or PETE.

Figure 7:
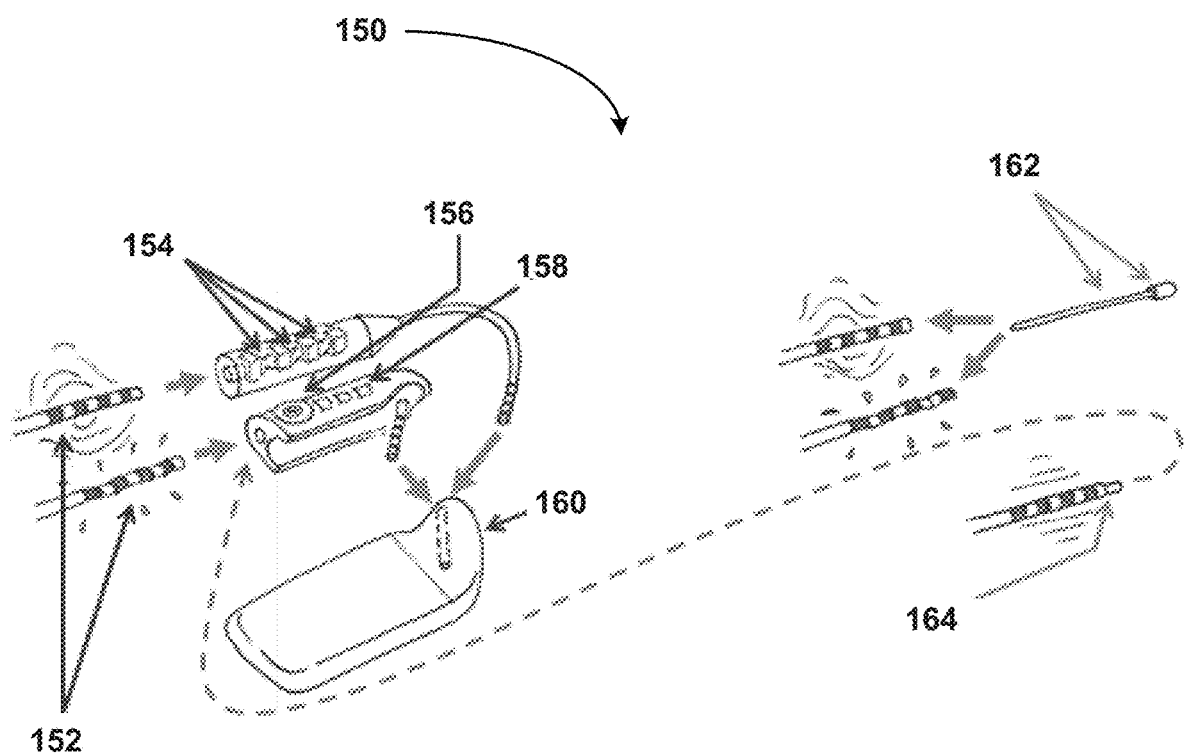
FIG. 7 is a conceptual diagram illustrating an example medical system, in accordance with one or more aspects of this disclosure.

FIG. 7 is a conceptual diagram illustrating a system 150, in accordance with one or more aspects of this disclosure. One or more components of system 150 may be secured to a patient using one or more fixation devices (e.g., fixation devices 12 or 30) described herein. In the example of FIG. 7, system 150 includes a lead connector 152, an integrated header 158, a IMD 160, and a short connector wire 162. Lead connectors 152 may the proximal end of a lead, include one or more electrical contacts, and may be flexible and too deformed to pass internal seals 154 inside a female end of an adaptor. Short connector wire 162 may consist of a wire connected to a handle or a one-piece injection molded plastic part. In some examples, short connector wire 162 may be constructed of insulated stainless steel or tungsten. A handle 164 of short connector wire 162 may be inserted in lead connector 152. Inserted short connector wire 162 may line-out (e.g., short some contacts together) and increase stiffness of an end of lead connector 152. Short connector wire 162 may be placed inside a lumen to line out contacts and stiffen lead connectors 152 before inserting the lead into an adaptor or integrated header 158.

Figure 8:
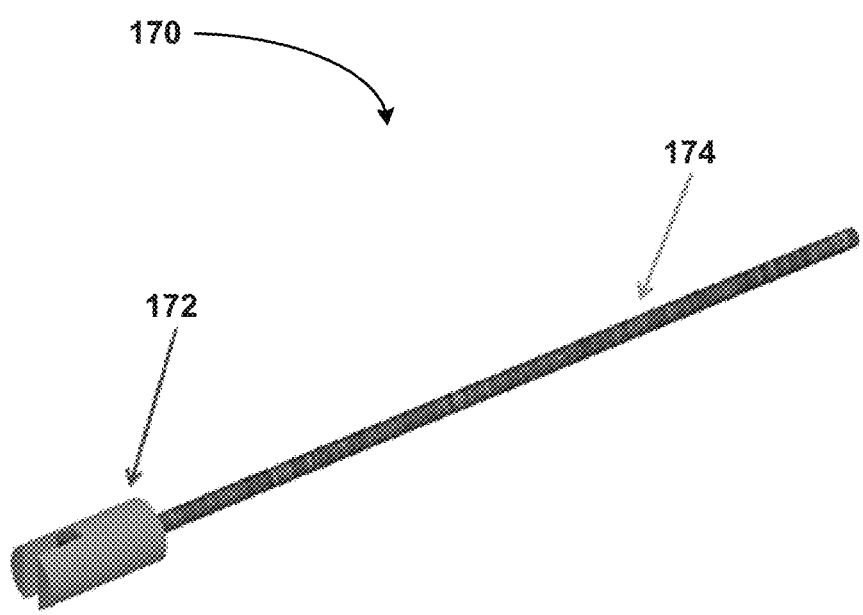
FIG. 8 is a conceptual diagram illustrating an example short connector wire, in accordance with one or more aspects of this disclosure.

FIG. 8 is a conceptual diagram illustrating an example short connector wire 170, in accordance with one or more aspects of this disclosure. Short connector wire 170 may include a wire 174 connected to a handle 172. In some examples, handle 172 may be attached or coupled to wire 174. For example, glue, heat seal, or other junction means may connect short connector wire 170 to handle 172. In some examples, short connector wire 170 may be constructed of metal, tungsten, or a plastic material. In some examples, by using a plastic wire inside the lead connector lumen, fluid penetration may be reduced, and impedance may be increased between internal contacts to facilitate the sensing feature of close loop DBS systems. In some examples, short connector wire 170 may be embedded into the adaptor such that the connection process will require the use of the stiffener by the user. For example, stiffener and embedded stiffener options include ethylene tetrafluoroethylene (ETFE) coated cable, guide wire, stylet wire, extruded polymer fiber, and torque tube (laser etched flexible elements). The guide-wire allows the extension, the coil portion of the guide-wire (the most flexible region) beyond any adaptor region with potential decrease concerns for flex fatigue damage to lead body, while still having a relatively stiff portion in the protected adaptor region to improve the ability to fully insert and withdraw the DBS lead connector in or out of the header.

Figure 9A:
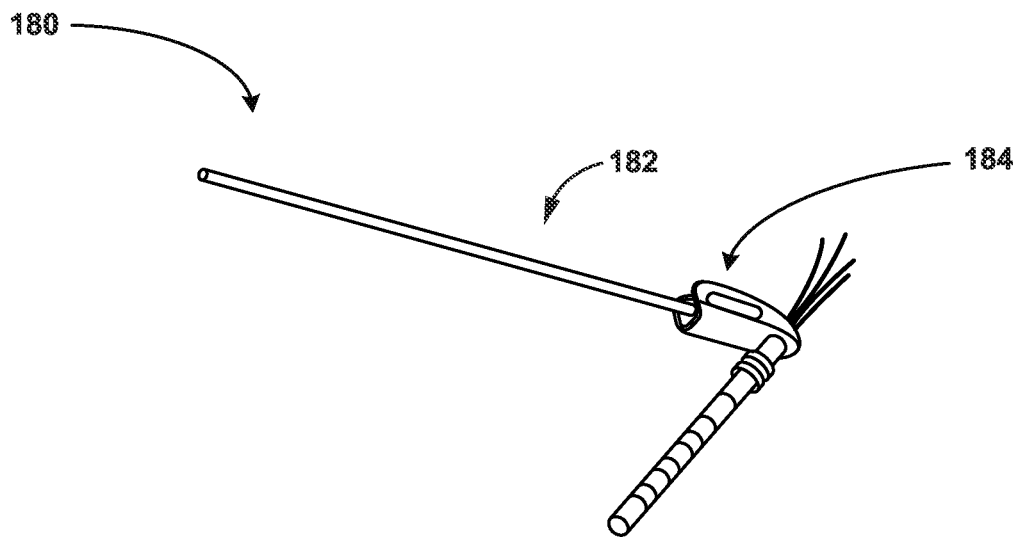
FIGS. 9A, 9B, and 9C are conceptual diagrams illustrating an example integrated header, in accordance with one or more aspects of this disclosure.
Figure 9B:
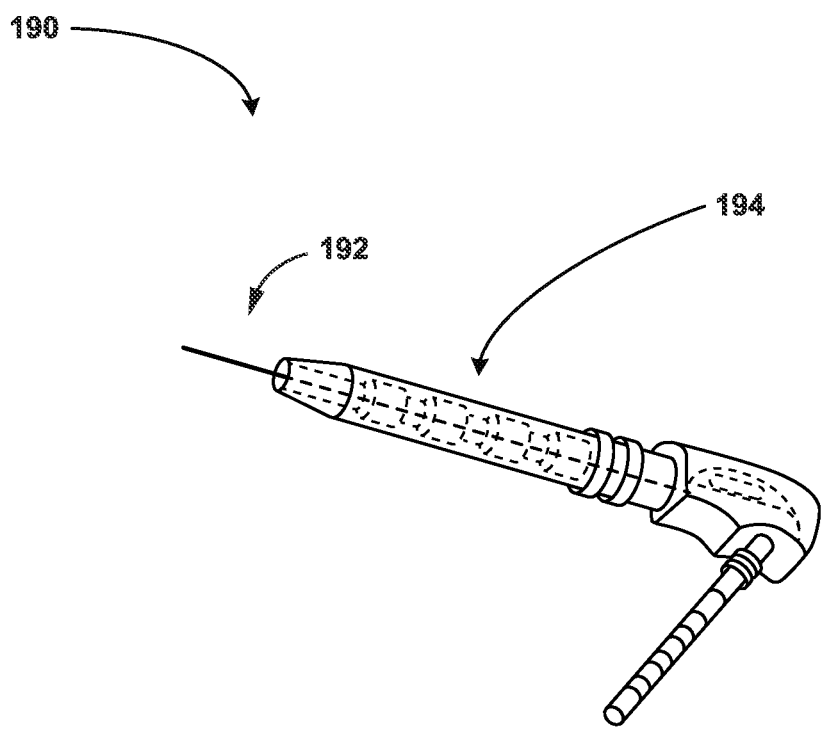
Figure 9C:
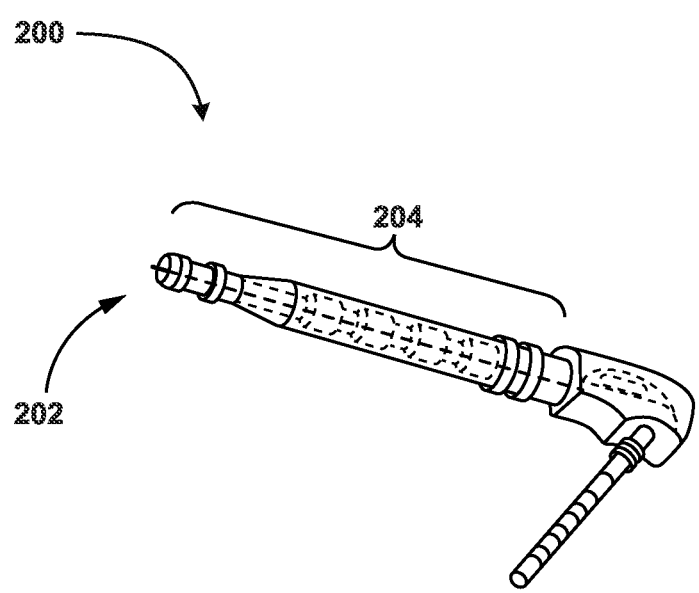

FIG. 9A is a conceptual diagram illustrating an example integrated header 180, in accordance with one or more aspects of this disclosure. A short stylet wire 182 is connected to a frame 184 prior to in-situ molding of a housing on integrated header 180. FIG. 9B is a conceptual diagram illustrating an example integrated header 190, in accordance with one or more aspects of this disclosure. Integrated header 190 may be similar to integrated header 180. A short stylet wire 192 is embedded within an in-situ molding housing 194. The distal end of short stylet wire 192 extends into distal housing end to ease insertion into a lumen of a lead to stiffen a lead end, line up contacts, and reduce current leakage. Reducing current leakage may be beneficial during replacement. In some examples, integrated header 190 may include a silicone rubber in-situ molded housing with embedded frame, insulated conductor cables, setscrew rings, and short stylet wire 192. FIG. 9C is a conceptual diagram illustrating an example integrated header 200, in accordance with one or more aspects of this disclosure. Integrated header 200 may be similar to integrated headers 180 and 190. The length of an embedded short stylet wire 204 may be such that the distal end of short stylet wire 204 may remain inside sealing boot 202. The female end of integrated header 200 may include sealing boot 202.

Figure 10A:
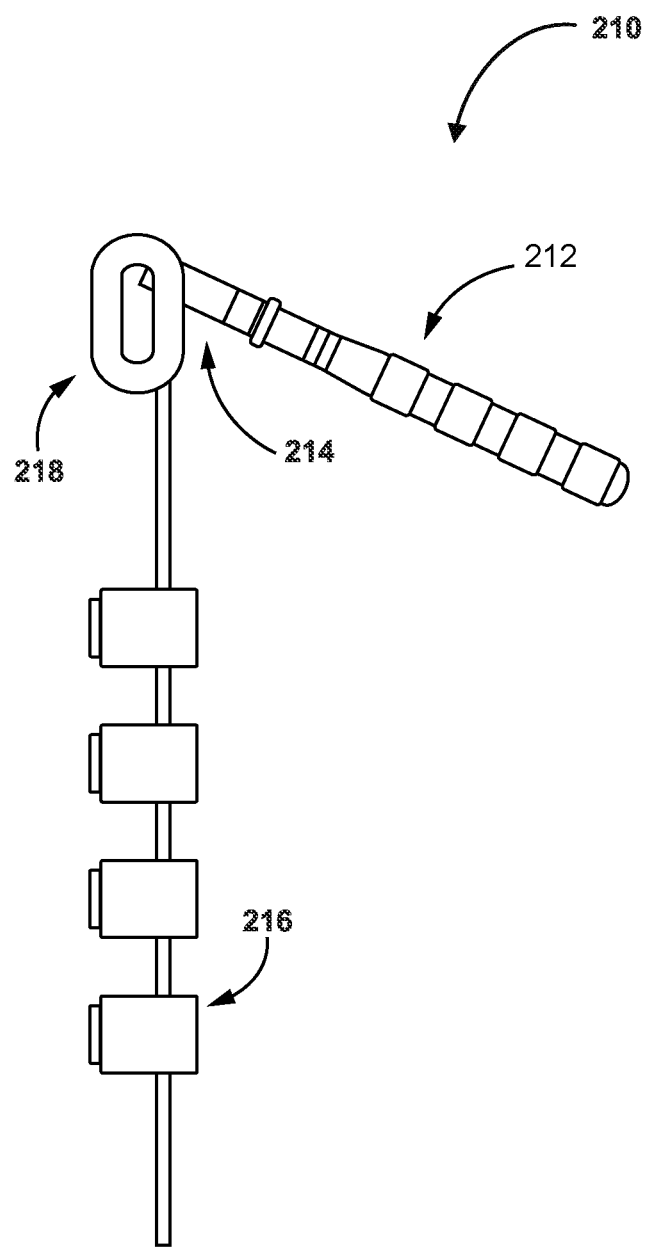
FIGS. 10A, 10B, 10C, and 10D are conceptual diagrams illustrating an example integrated header, in accordance with one or more aspects of this disclosure.
Figure 10B:
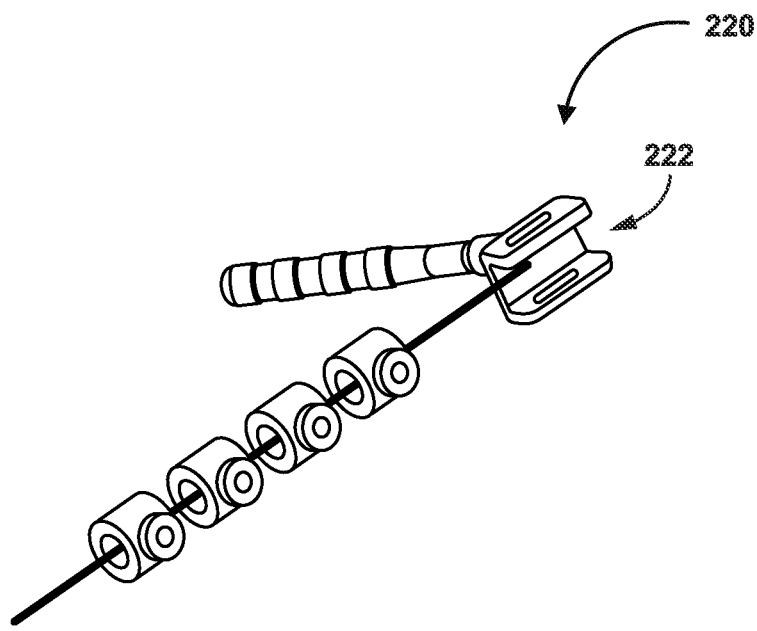
Figure 10C:
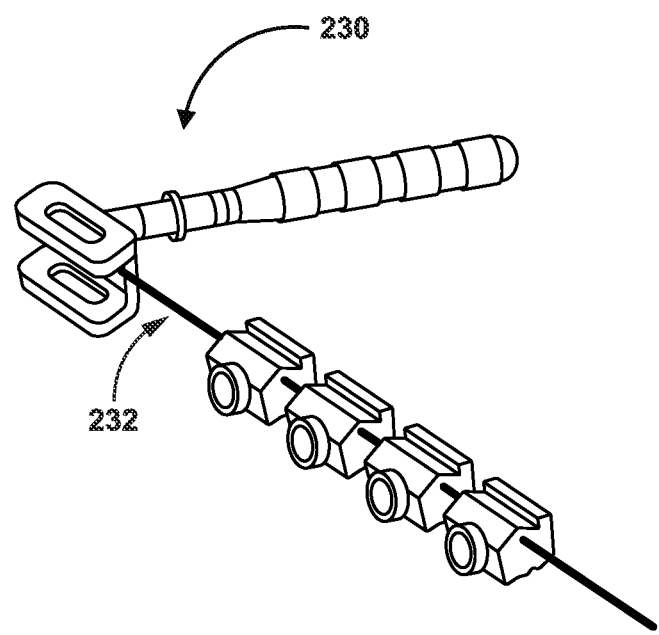
Figure 10D:
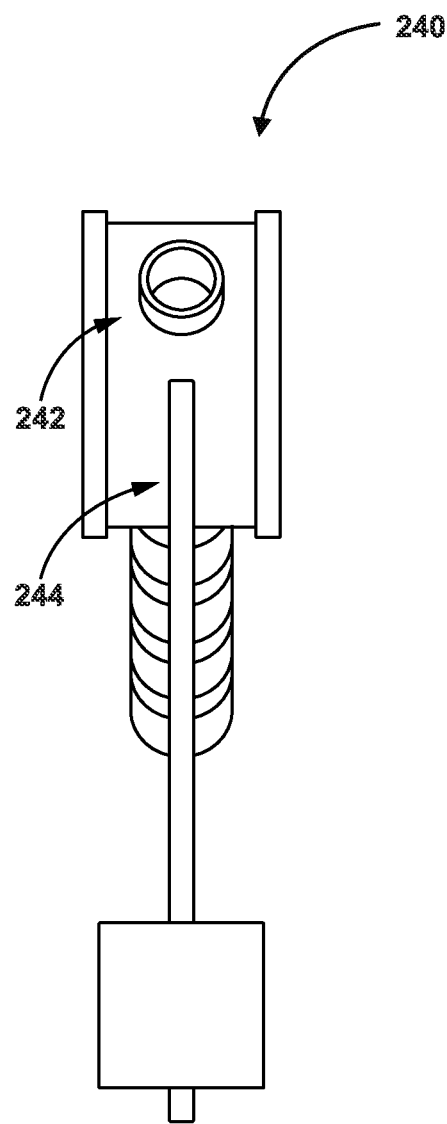

FIG. 10A is a conceptual diagram illustrating an example integrated header 210, in accordance with one or more aspects of this disclosure. In the example of FIG. 10A, integrated header 210 includes a male end 212, a distal floating connector ring 214, a setscrew contacts/blocks 216, and a frame 218. Male end 212 may include an inside tube and four insulated conductor cables. Distal floating connector ring 214 may have varying lengths. FIG. 10B is a conceptual diagram illustrating an example integrated header 220, in accordance with one or more aspects of this disclosure. Integrated header 220 may be similar to integrated header 210. Insulated conductor cables 222 inside male end 212 may run through gutter of frame 218 towards setscrew contacts/blocks 216. FIG. 10C is a conceptual diagram illustrating an example integrated header 230, in accordance with one or more aspects of this disclosure. Integrated header 230 may be similar to integrated headers 210 and 220. Integrated header 230 includes a short connector/stylet wire 232. FIG. 10D is a conceptual diagram illustrating an example integrated header 240, in accordance with one or more aspects of this disclosure. Integrated header 240 may be similar to integrated headers 210, 220, and 230. Integrated header 240 includes a longer distal floating ring laser 242 welded to frame 218 and a short connector/stylet wire welded 244 to frame 218.

Figure 11A:
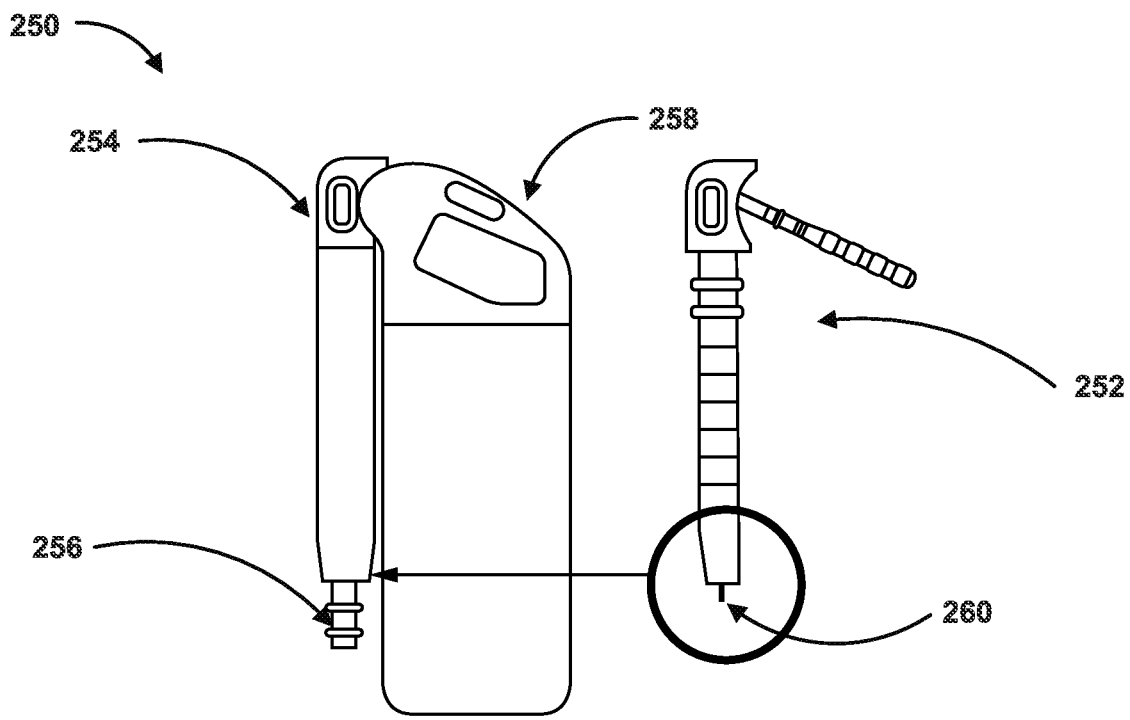
FIGS. 11A and 11B are conceptual diagrams illustrating an example medical system, in accordance with one or more aspects of this disclosure.
Figure 11B:
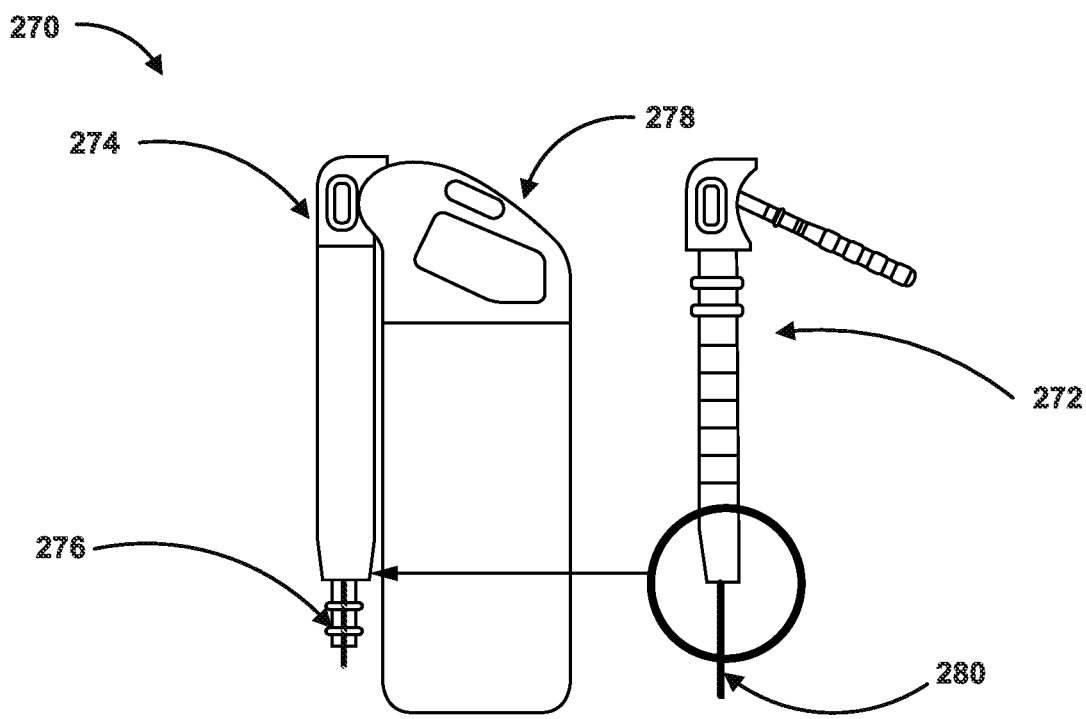

FIG. 11A is a conceptual diagram illustrating an example system 250, in accordance with one or more aspects of this disclosure. System 250 includes a refined integrated header 252, a housing 254, a sealing boot 256, a medical device 258, and a short connector/stylet wire 260. FIG. 11B is a conceptual diagram illustrating an example system 270, in accordance with one or more aspects of this disclosure. System 270 includes a refined integrated header 272, a housing 274, a sealing boot 276, a medical device 278, and a short connector/stylet wire 280. System 270, excluding short connector/stylet wire 280, may be similar to system 250. In some examples, as shown in FIG. 11A, short connector/stylet wire 260 may extend distal from the female end of refined integrated header 252 to be able to start moving the lead connector over short connector/stylet wire 260. In some examples, short connector/stylet wire 260 may be relatively short in length to avoid interference with bending of lead when leaving recessed area, e.g., a recessed bone/skull chamber. In other examples, as shown in FIG. 11B, stylet wire 280 may extend too far from refined integrated header 272 in system 270 and may interfere with bending of lead when leaving recessed area.

Figure 12:
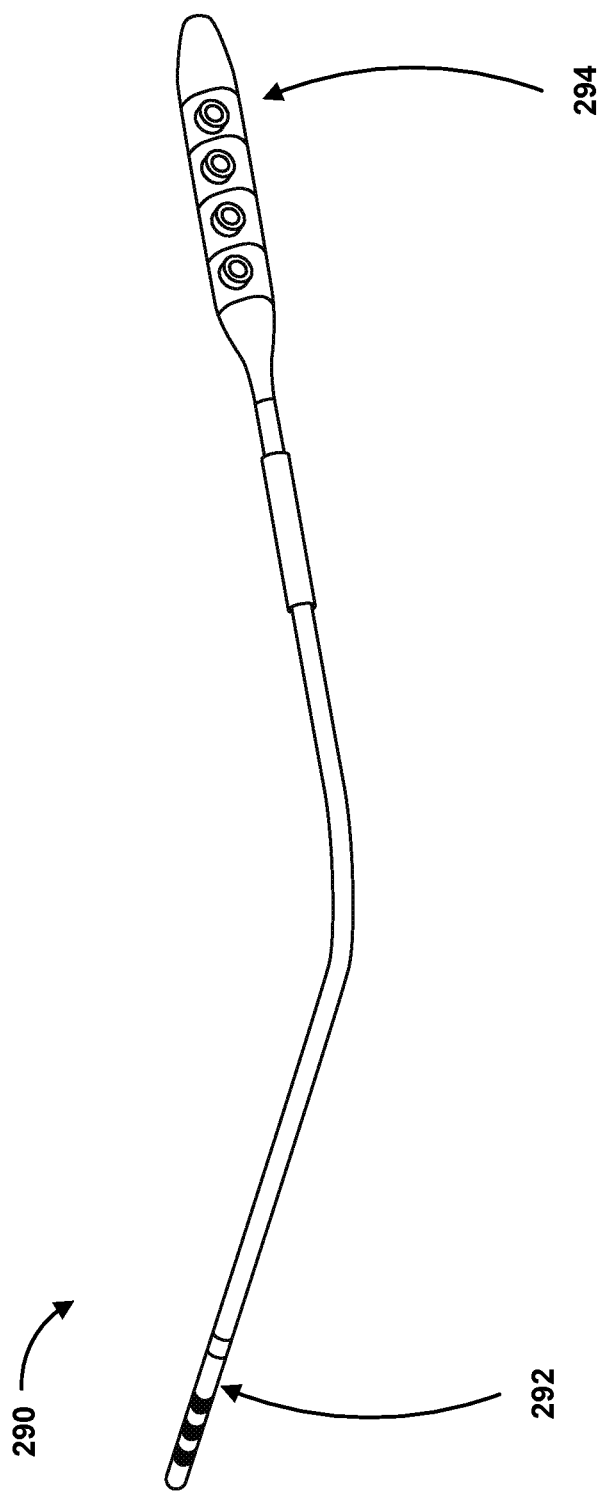
FIG. 12 is a conceptual diagram illustrating an example pigtail extension connector, in accordance with one or more aspects of this disclosure.

FIG. 12 is a conceptual diagram illustrating an example pigtail extension connector 290, in accordance with one or more aspects of this disclosure. In the example of FIG. 12, pigtail extension connector 290 includes a male end 292 and a female end 294. Male end 292 may be a lead or an extension. In some examples, female end 294 may be a standard commercial eight-to-four DBS extension (no internal sealings) or a restricted eight-to-four DBS extension (internal sealings to support sensing). Female end 294 may match with a sealing boot (not shown). In some examples, a standard commercial eight-to-four DBS extension may be used because it relies on a proven fitment of a fragile DBS lead connector for new implants as well as for replacements for a deformed lead connector.

Figure 13A:
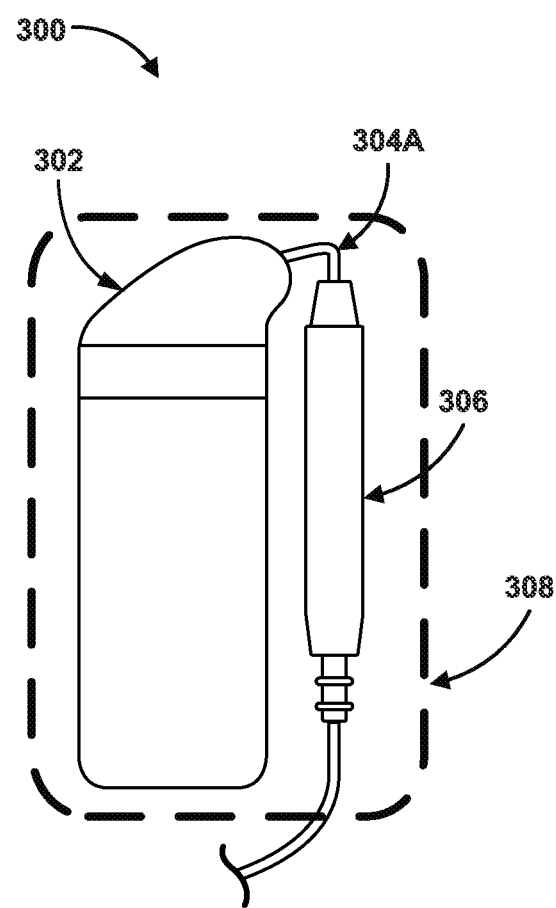
FIGS. 13A, 13B, and 13C are conceptual diagrams illustrating an example medical system, in accordance with one or more aspects of this disclosure.
Figure 13B:
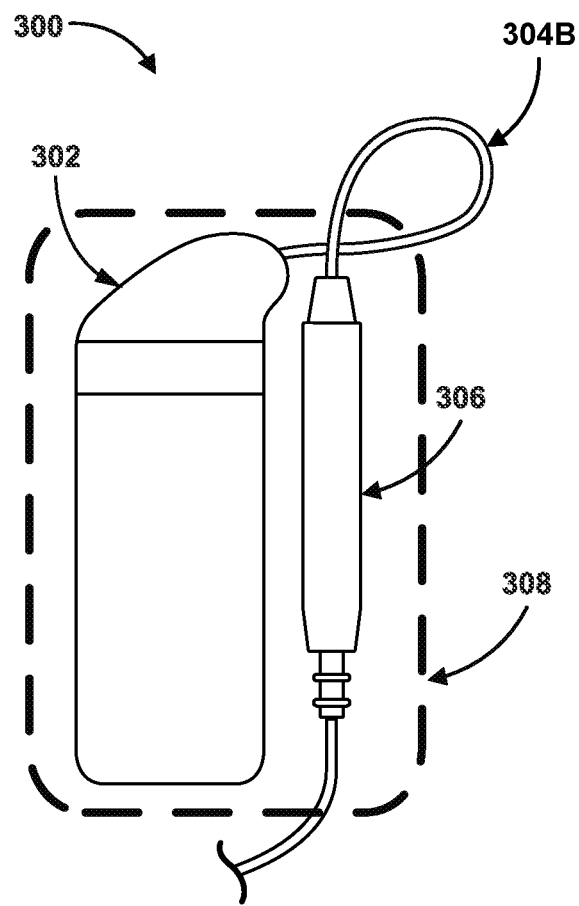
Figure 13C:
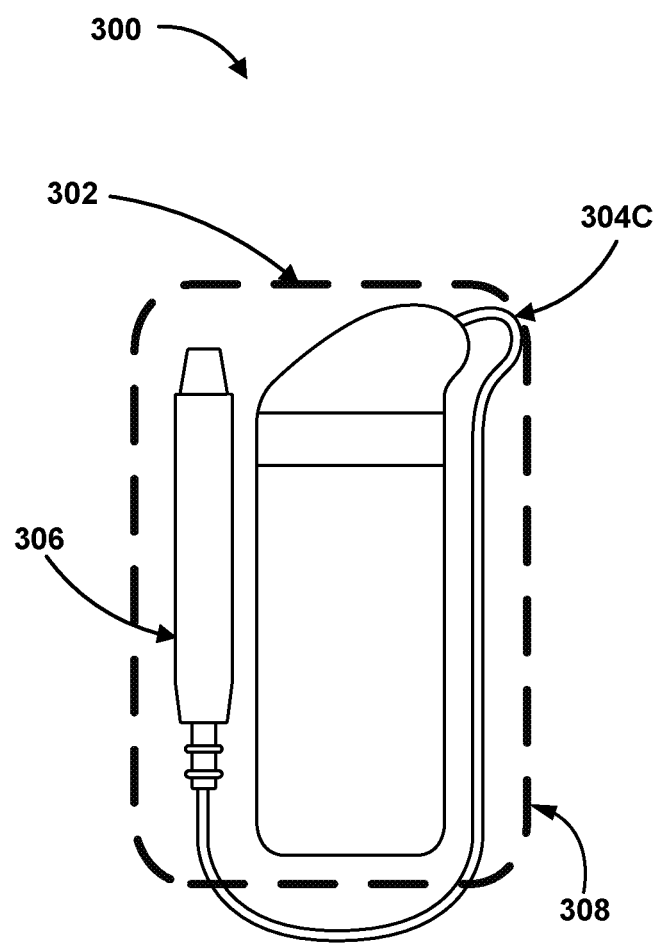

FIGS. 13A-13C are conceptual diagrams illustrating an example system 300, in accordance with one or more aspects of this disclosure. In the examples of FIGS. 13A-13C, system 300 includes a IMD 302, pigtail extensions 304A-304C, an adaptor 306, and a recessed area of cranium 308. In FIG. 13A, the male end of pigtail extension 304A may be bent to fit recessed area of cranium 308, if recessed area of cranium 308 is not enlarged. In FIG. 13B, male end of pigtail extension 304B may be looped out and back inside recessed area of cranium 308, if recessed area of cranium 308 is not enlarged. In FIG. 13C, male end of pigtail extension 304C may be bent in order to fit inside recessed area of cranium 308 if recessed area of cranium 308 is not enlarged. As shown in FIG. 13C, looping pigtail extension 304C around the IMD 302, such as an INS, may need a larger recessed area of cranium 308. In some examples, a user, such as a clinician, may check feasibility to backfill male end of pigtail extension 304A-304C with epoxy in a bent shape instead of straight shape to reduce the bending radius of pigtail extension 304C without an increased risk of damage for the conductors in the extension.

Figure 14D:
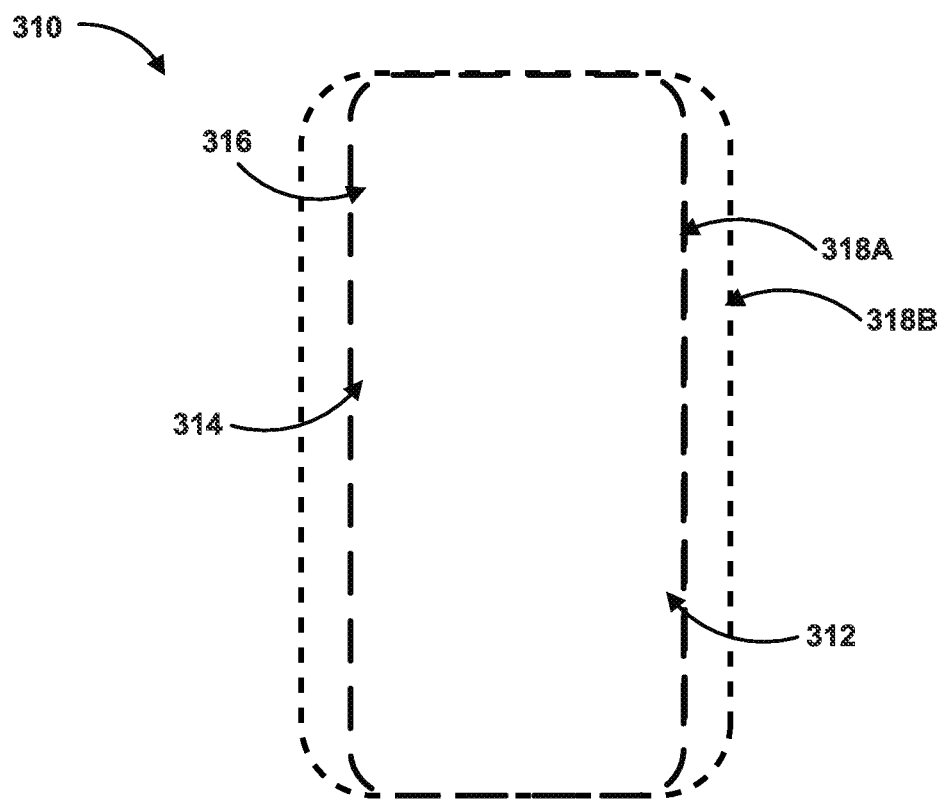
Figure 14E:
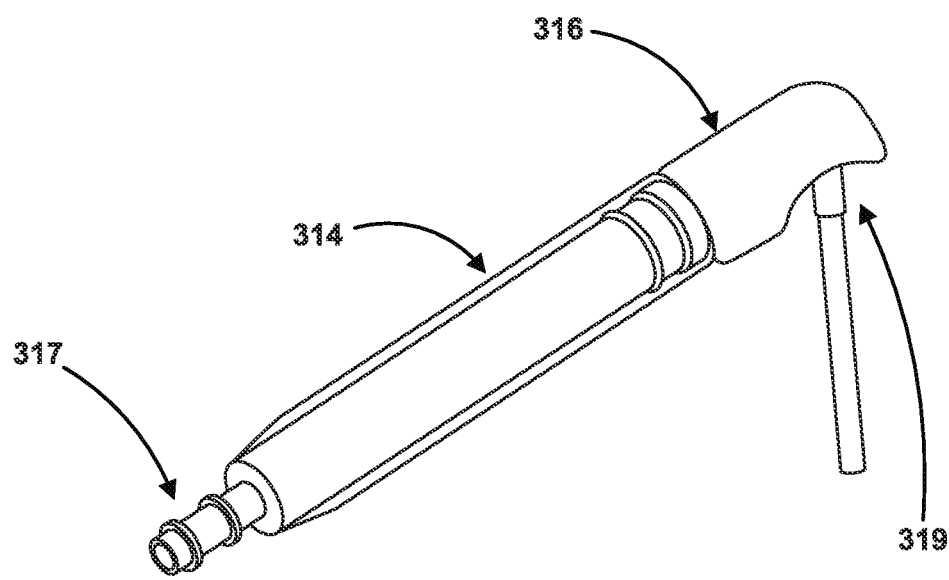
Figure 14F:
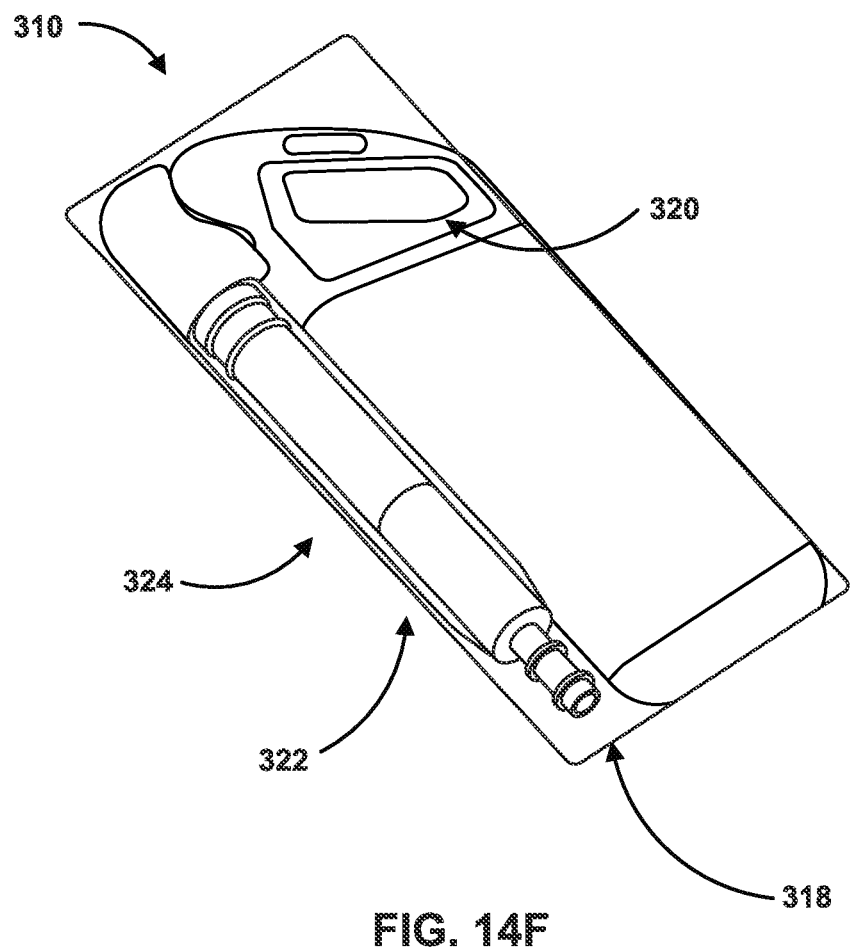

FIG. 14A-14F are conceptual diagrams illustrating an example system 310, in accordance with one or more aspects of this disclosure. System 310 may be similar to systems 250 and 270. System 310 may be used with system 10 of FIG. 1A. In the example of FIG. 14A, system 310 includes a IMD 312, an adaptor 314 that accepts a lead, and a header 316. IMD 312 may be an INS. FIG. 14B provides a side perspective of system 310, and FIG. 14C provides a side perspective of 310, which is the opposite side of the side shown in FIG. 14B. In the example of FIG. 14D, system 310 is shown being disposed in a recessed area of cranium 318A. The depth and size of recessed area of cranium 318A remains relatively small because no material is added over IMD 312 or adaptor 314. In some examples, recessed area of cranium 318A may be enlarged to recessed area of cranium 318B in order to accommodate pigtail extensions or material over IMD 312 or adaptor 314. The example of FIG. 14E includes adaptor 314, header 316, extension female connector 317 with a sealing boot configured to accept a proximal end of a lead, and a male connector 319 configured to couple to IMD 312. In the example of FIG. 14F, system 310 includes a connector hump 320 on IMD 312, a circular plate 322, and an attachment mechanism 324. IMD 312 may be placed in recessed area of cranium 318 and fixated by circular plate 322 and one attachment mechanism 324, such as a bone screw. IMD 312 may include connector hump 320 configured to level with, or on the same plane as, circular plate 322 after implantation. Circular plate 322 may be constructed with non-conductive materials, such as one or more polymers.

Figure 15A:
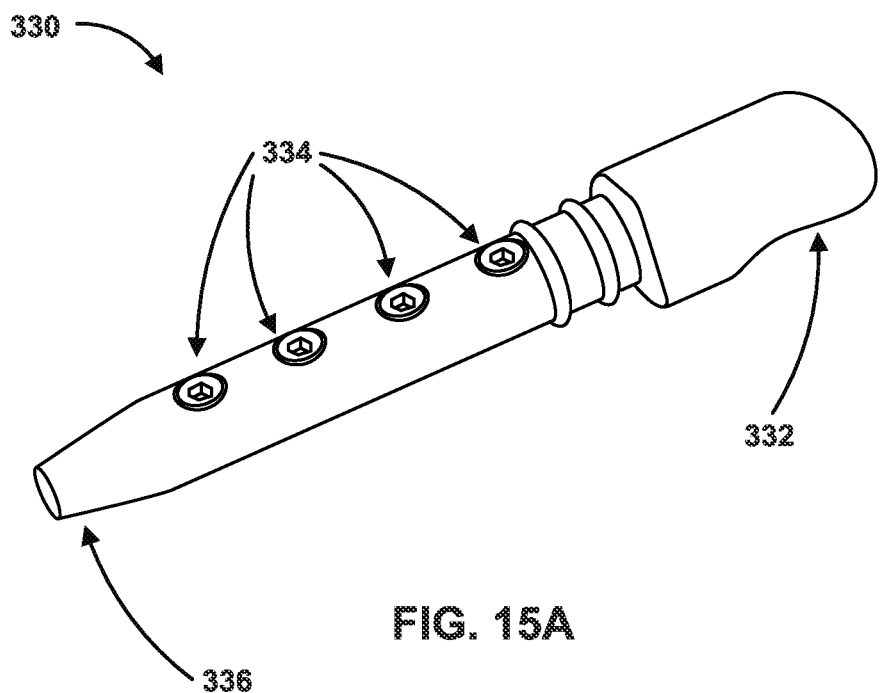
FIGS. 15A and 15B are conceptual diagrams illustrating an example medical system, in accordance with one or more aspects of this disclosure.
Figure 15B:
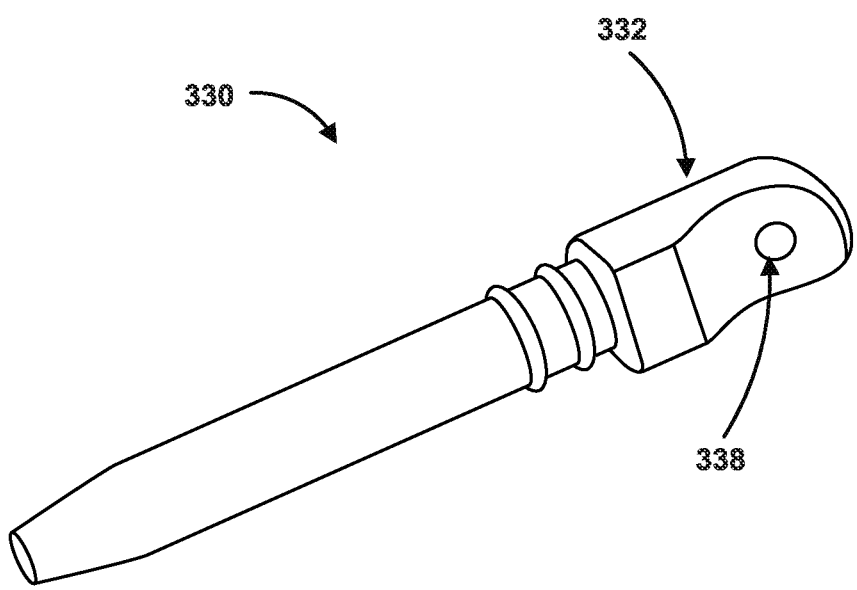

FIGS. 15A and 15B are conceptual diagrams illustrating an example system 330, in accordance with one or more aspects of this disclosure. In the examples of FIGS. 15A and 15B, system 330 includes a header 332, setscrews 334, and a sealing boot 336, and defines a hole 338. FIG. 15A displays an example of four setscrews 334 with sealing boot 336 for use on DBS leads for new implants and replacements. FIG. 15B displays system 330 for three-dimensional printing purposes. For three-dimensional printing purposes, system 330 may have hole 338 inside housing of header 332 that is configured to accept, and glue, for example, a male lead connector to header 332.

FIGS. 16A-16C are conceptual diagrams illustrating an example system 340, in accordance with one or more aspects of this disclosure. In the examples of FIGS. 16A-16C, system 340 includes a header 342, an adaptor 344, and a IMD 346. Header 342 may be constructed of various materials including silicone, and a connector of header 342 may be inserted into a passage defined by IMD 346. In some examples, IMD 346 may be an INS. In FIGS. 16A-16C, header 342 may be an alternative for short pigtail extensions. In some examples, a recessed area on a cranium may remain small because no material is added over adaptor 344 or IMD 346.

Figure 17A:
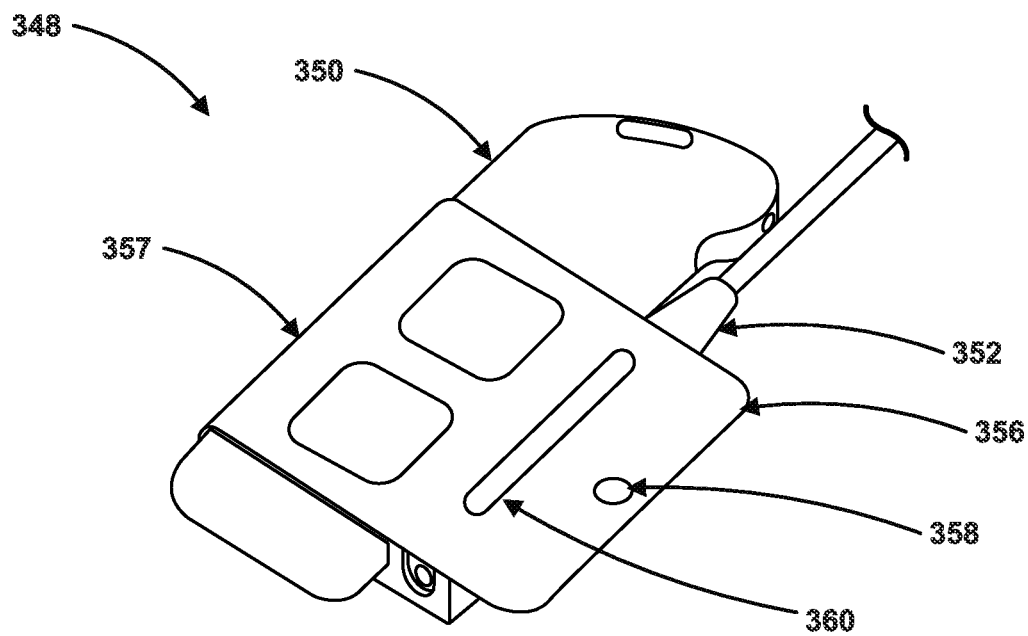
FIGS. 17A, 17B, 17C, 17D, 17E, 17F, 17G, 17H, 17I, and 17J are conceptual diagrams illustrating an example medical system, in accordance with one or more aspects of this disclosure.
Figure 17B:
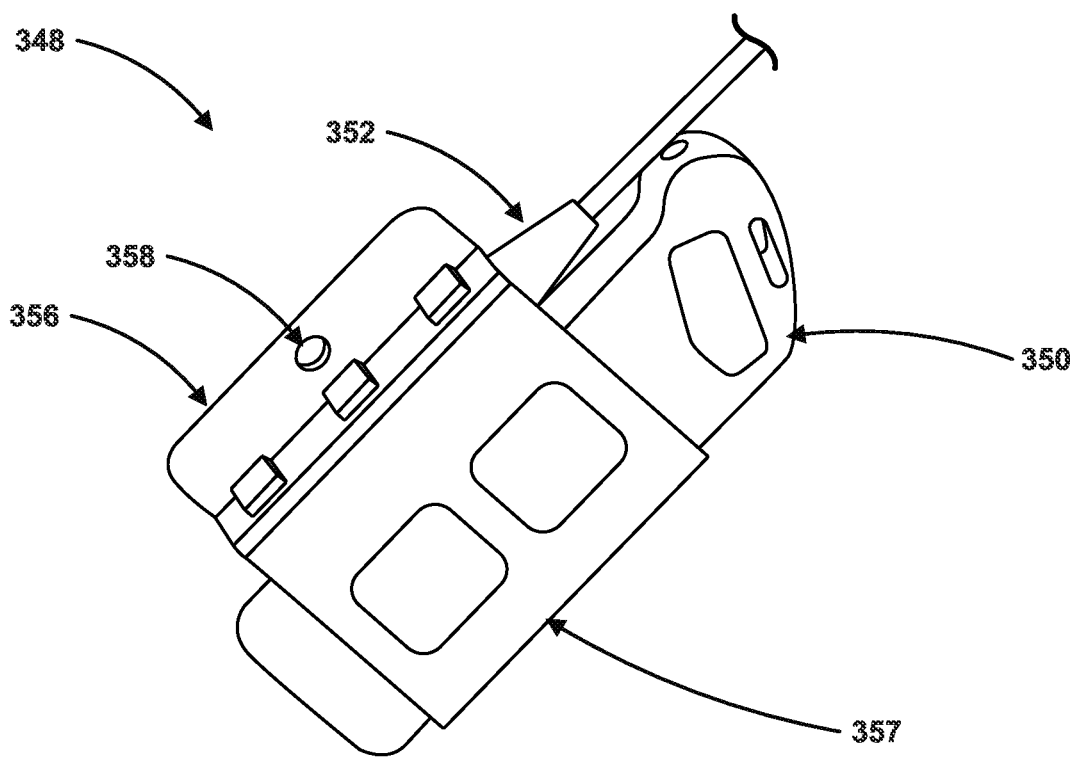
Figure 17C:
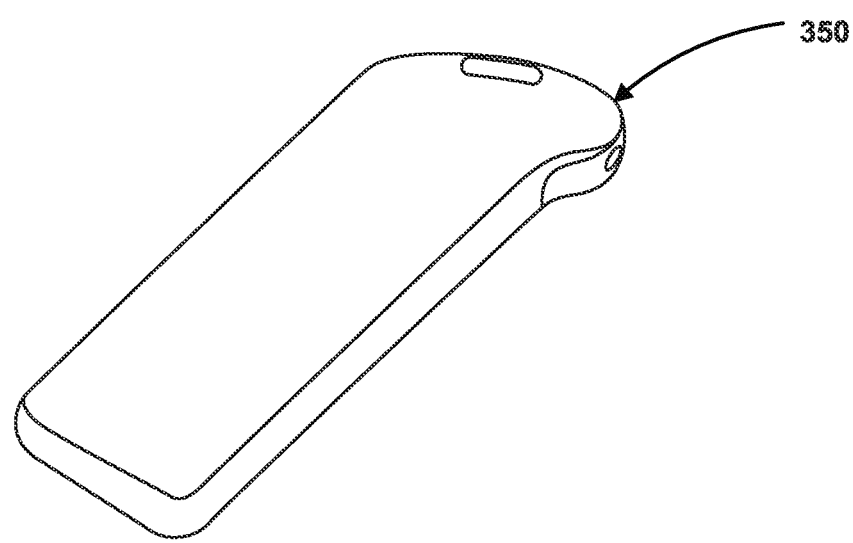
Figure 17D:
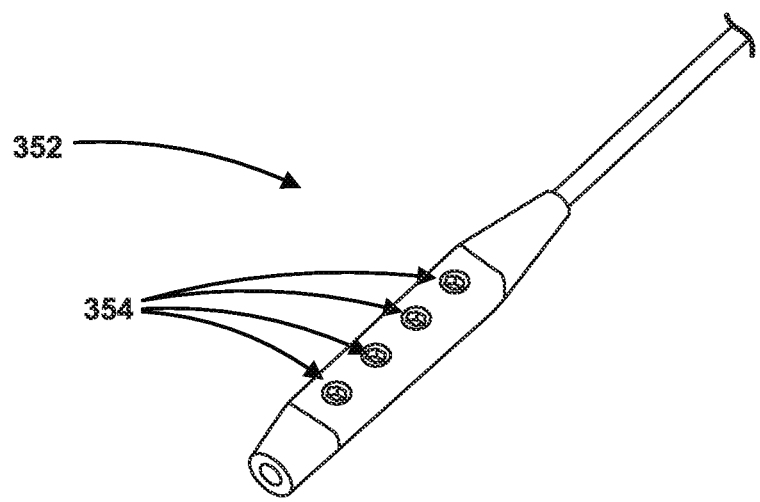
Figure 17E:
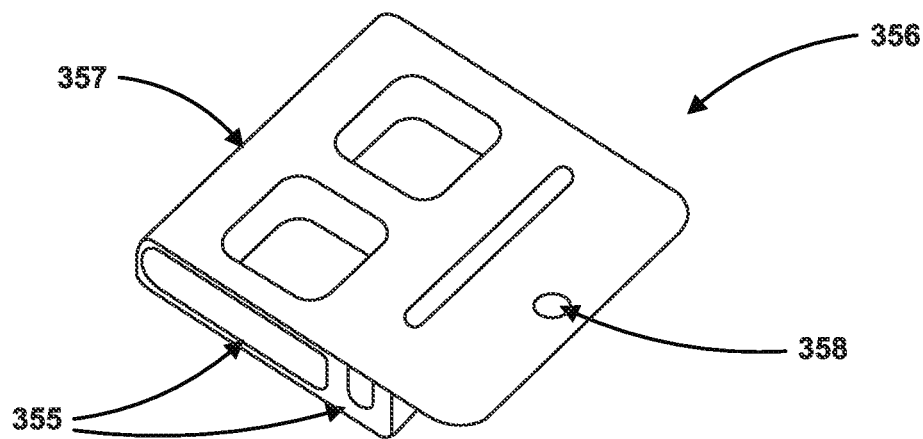
Figure 17F:
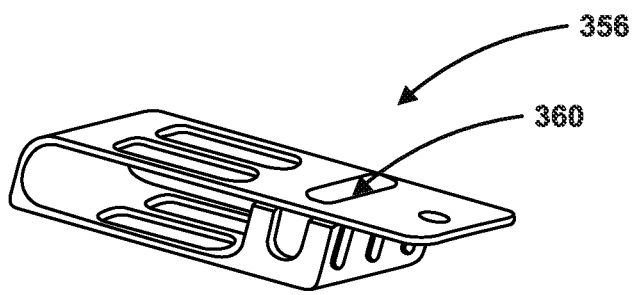
Figure 17G:
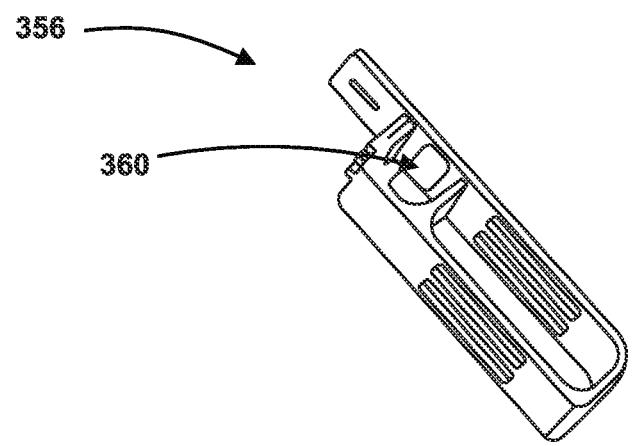
Figure 17H:
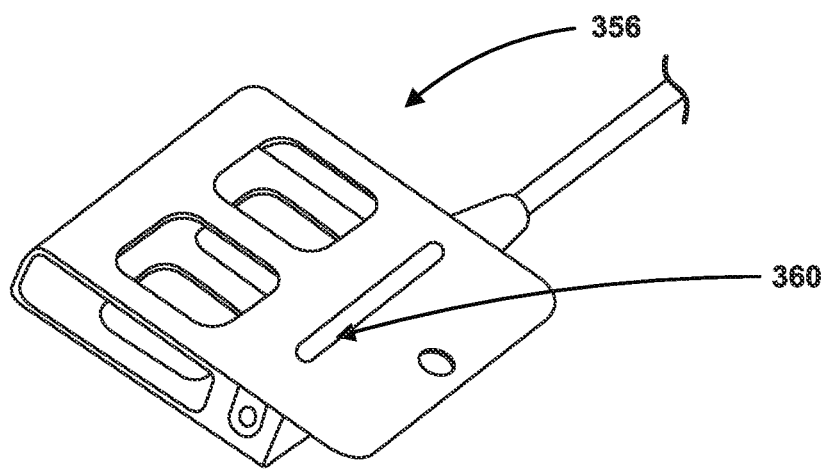
Figure 17I:
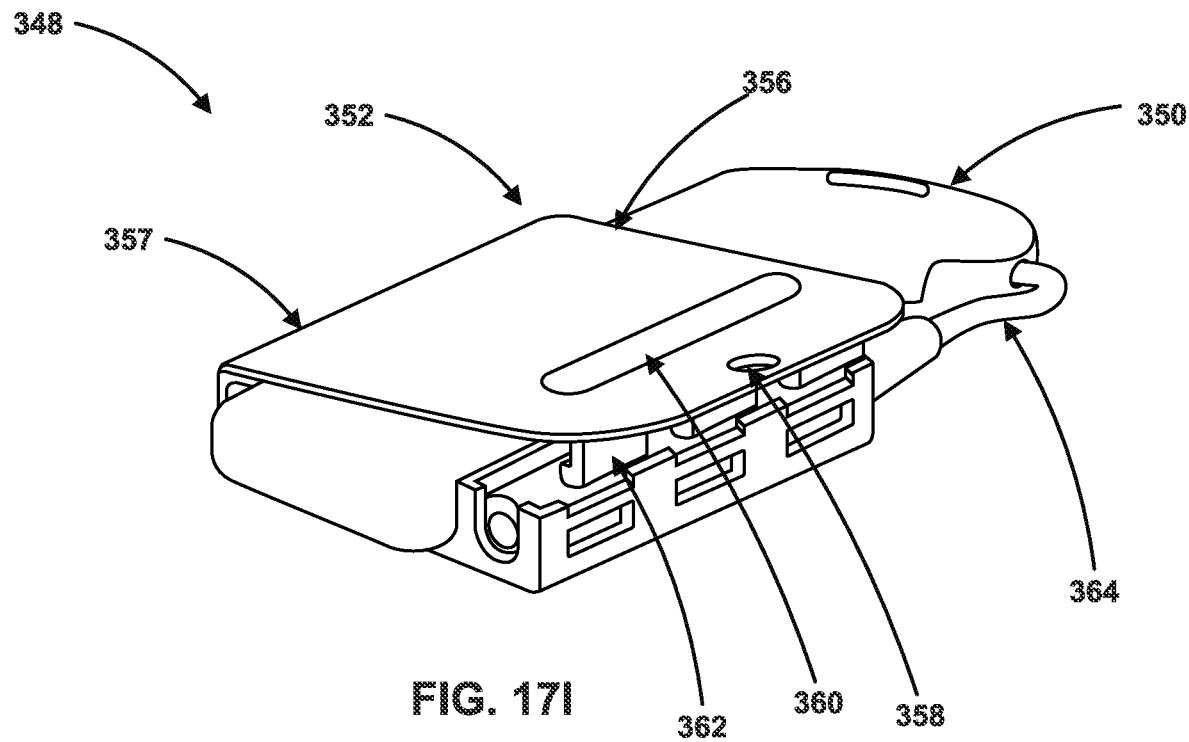
Figure 17J:
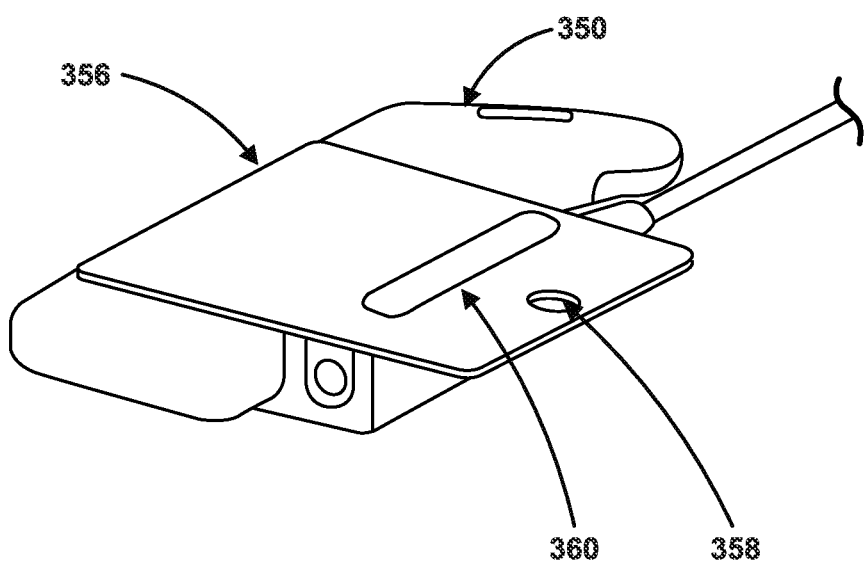

FIGS. 17A-17J are conceptual diagrams illustrating an example system 348, or portions of example system 348, in accordance with one or more aspects of this disclosure. In the examples of FIGS. 17A and 17B, system 348 includes a cranial INS 350, an adaptor 352, a clamp 356 with a hinge 357, and a bone screw fixation hole 358. FIGS. 17A and 17B display system 348 from two different perspectives. Clamp 356 is configured to accept and secure INS 350 and adaptor 352 to the cranium. FIG. 17C illustrates cranial INS 350. FIG. 17D illustrates an adaptor 352 with four setscrews 354. FIG. 17E displays clamp 356 with two separated cavities 355, one cavity for cranial INS 350 and another cavity for adaptor 352, and defining bone screw fixation hole 358. FIGS. 17F-17H display three perspectives of a silicone rubber inlay 360 of hinged clamp 356. Silicone rubber inlay 360 may seal port holes of setscrew 354 against fluid leakage after tightening setscrews 354. In the example of FIG. 17I, system 348 includes snap arms 362 to close clamp 356. Hinge 357 may help keep the lid of clamp 356 down in a closed position. FIG. 17I displays clamp 356 in a partially open configuration. The male end of an adaptor 364 fits in an INS socket on the patient, e.g., an INS recess in the cranium. FIG. 17J displays clamp 356 in the closed position.

Figure 18:
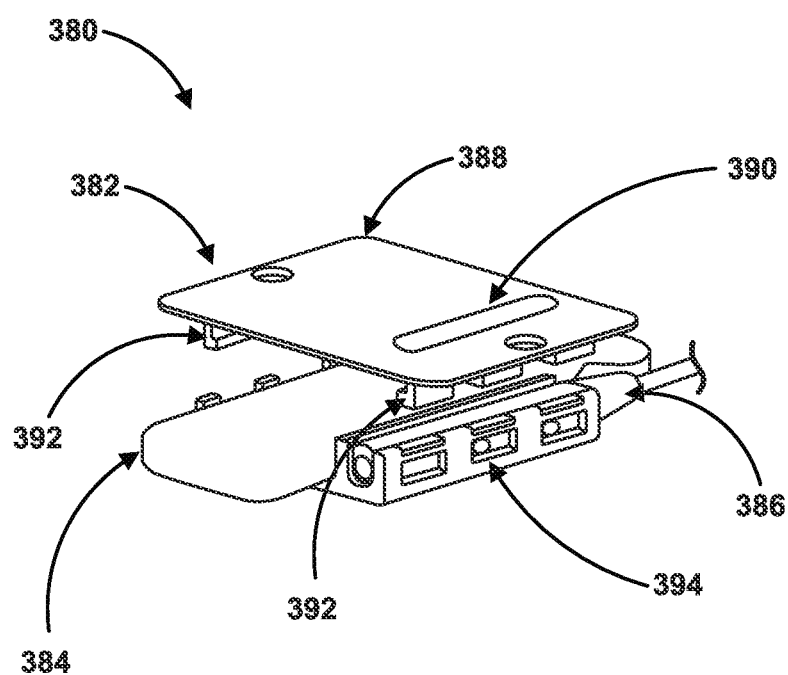
FIG. 18 is a conceptual diagram illustrating an example medical system, in accordance with one or more aspects of this disclosure.

FIG. 18 is a conceptual diagram illustrating an example system 380, in accordance with one or more aspects of this disclosure. In the example of FIG. 18, system 380 includes a two-piece clamp 382, a cranial INS 384, and an adaptor 386 configured to couple with IMD 384. Two-piece clamp 382 includes a lid 388, a silicone rubber inlay 390, snap arms 392, and a cup 394. Snaps 392 may lock lid 388 on cup 394. Silicone rubber inlay 390 may seal the setscrew port holes of adaptor 386 against two-piece clamp 382 to prevent leakage after tightening the setscrews on adaptor 386.

Figure 19A:
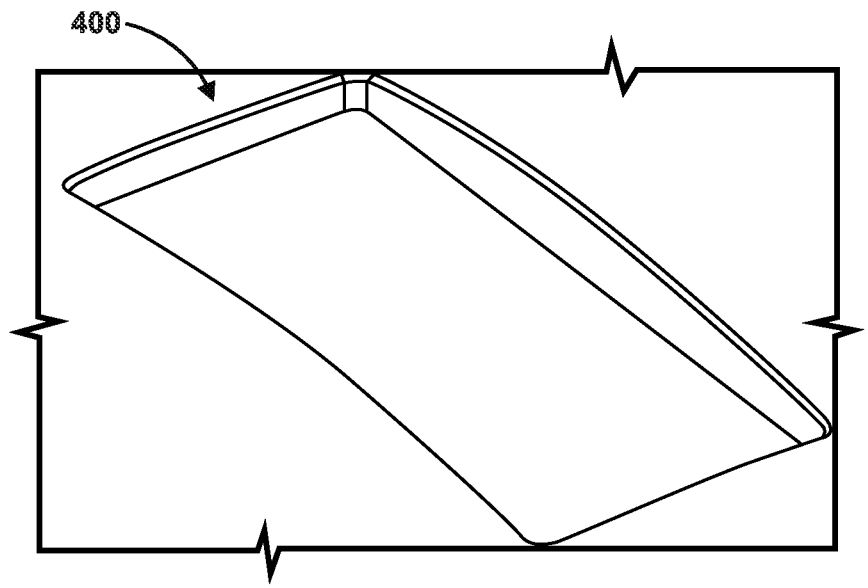
FIGS. 19A, 19B, 19C, 19D, 19E, 19F, 19G, and 19H are conceptual diagrams illustrating an example medical system, in accordance with one or more aspects of this disclosure.
Figure 19B:
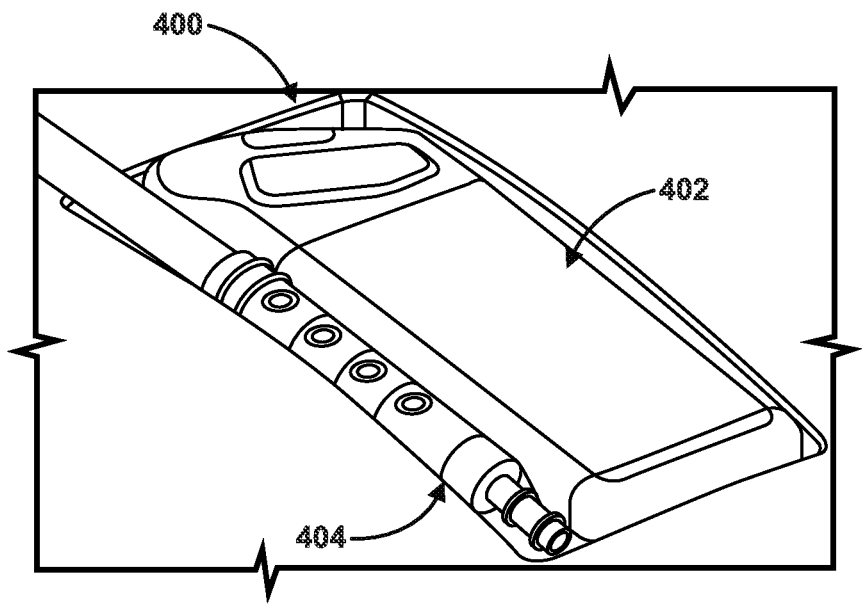
Figure 19C:
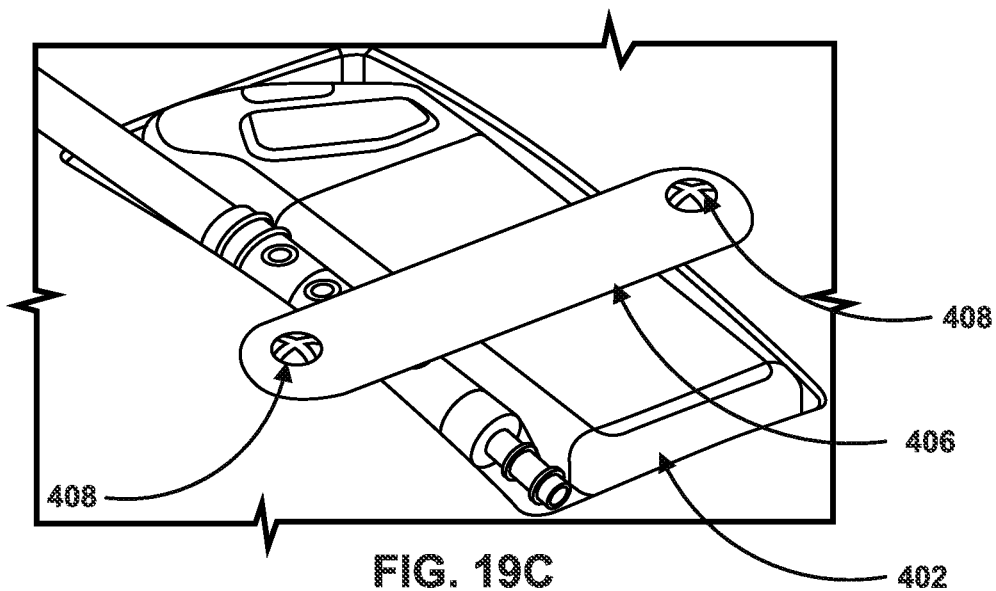
Figure 19D:
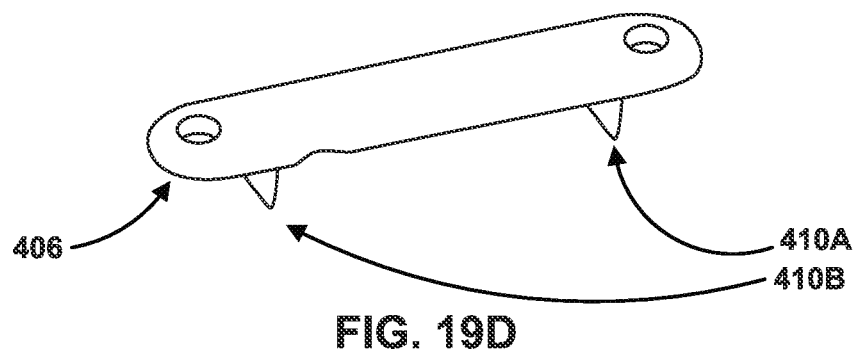
Figure 19E:
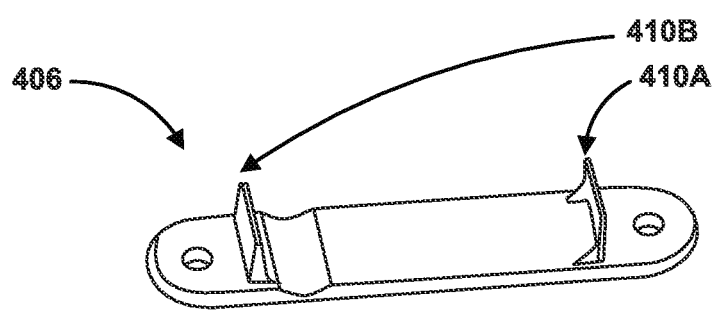
Figure 19F:
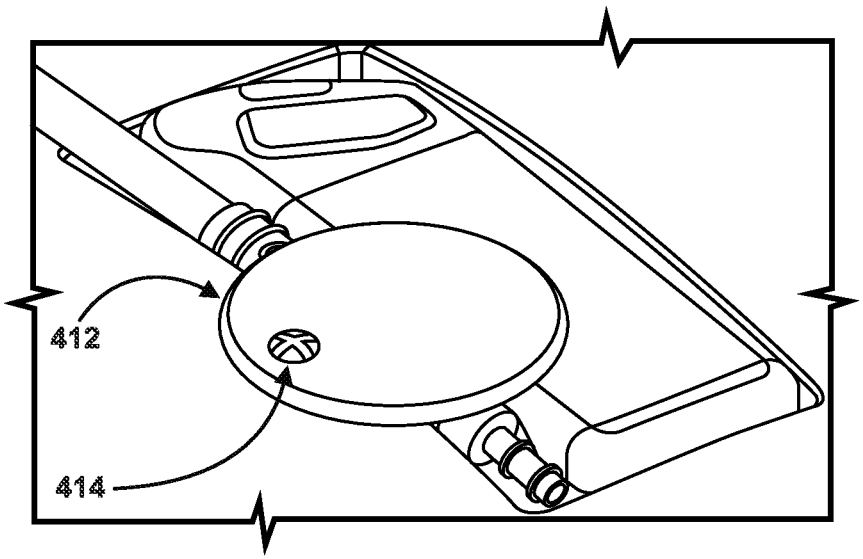
Figure 19G:
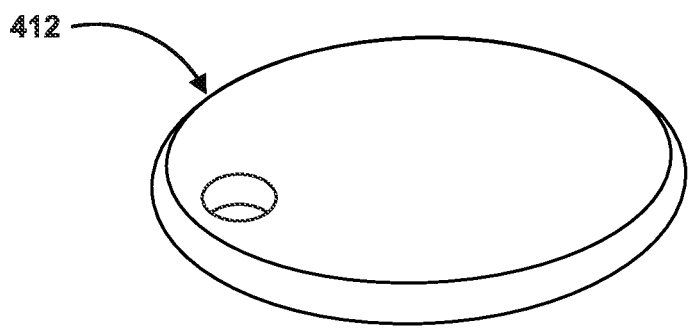
Figure 19H:
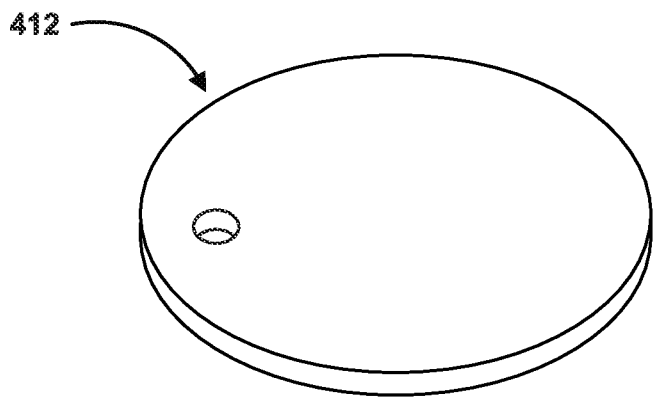

FIG. 19A is a conceptual diagram illustrating an example recessed area 400, in accordance with one or more aspects of this disclosure. In the example of FIG. 19A, recessed area 400 is in a cranium. FIG. 19B illustrates a cranial INS 402 and a female end of an adaptor 404 placed inside recessed area 400 of a cranium. FIG. 19C illustrates cranial INS 402 and adaptor 404 being retained within recessed area 400 by a plate 406 with two bone screws 408. Plate 406 may be formed into various shapes and sizes, including a rectangular shape with rounded corners as shown in the example of FIG. 19A. Plate 406 may be constructed of a polymer or some other non-electrically conductive materials in some examples. FIG. 19D illustrates a top view of plate 406, and FIG. 19E illustrates a bottom view of plate 406. Plate 406 may have small bridges 410A and 410B underneath to hold cranial INS 402 and adaptor 404 together. Bridges 410 may also have or include one or more lips or snaps to secure to INS 402 and/or adapter 404. In some examples, the addition of bridges 410 to plate 406 may increase the size of recessed area 400. Plate 406 may be configured to receive one or more bone screws 408 and may be formed into various shapes and sizes, including rectangular or oval shapes. FIG. 19F illustrates how plate 412 may be circular and may have only one bone screw 414. Plate 412 may be similar to plate 406 and may have one or more bone screws 414 and may be formed into various shapes and sizes. In some examples, one bone screw 414 may be easier to place next to a recessed chamber. In some examples, the rigidity of plate 412 and clamping force of one bone screw 414 may be sufficient to hold down a cranial INS. Plate 412 may extend over recessed area and cranial INS an extent sufficient to hold cranial INS in place over an extended period of time. The example shown in FIG. 19F may be similar to the example shown in FIG. 14F. FIG. 19G is top view of plate 412 that faces away from the cranium, and FIG. 19H is a bottom view of plate 412 that faces towards the cranium.

Figure 20:
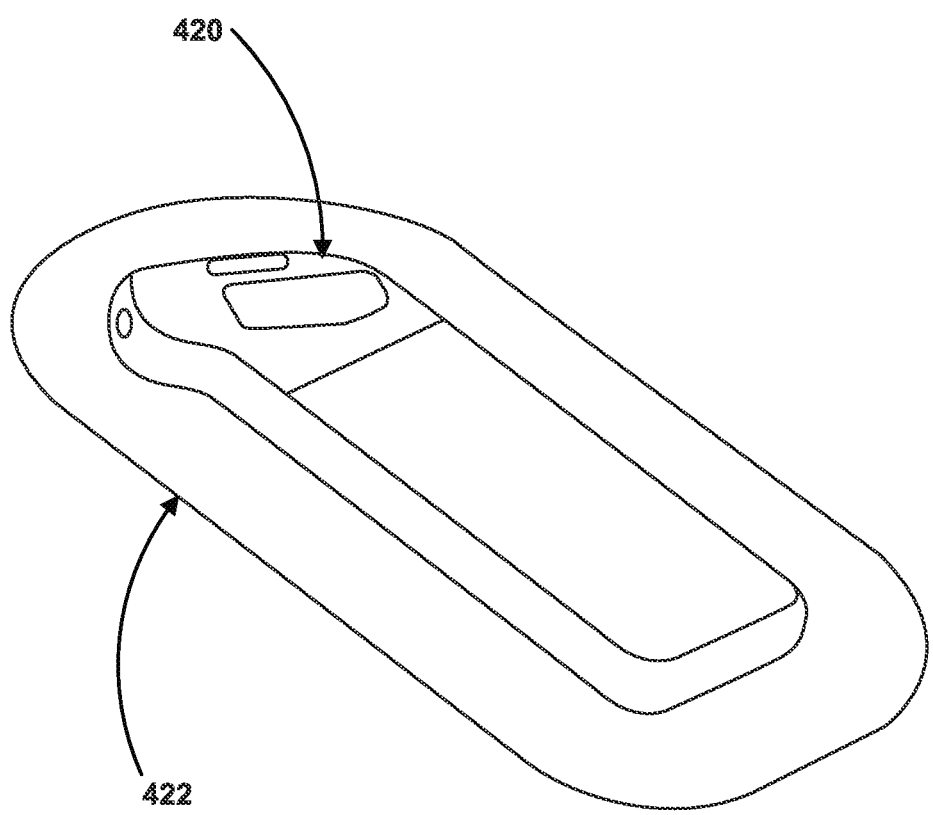
FIG. 20 is a conceptual diagram illustrating an example medical device, in accordance with one or more aspects of this disclosure.

FIG. 20 is a conceptual diagram illustrating an example cranial INS 420, in accordance with one or more aspects of this disclosure. In the example of FIG. 20, cranial INS 420 may have an accessory 422. In some examples, accessory 422 may be attached to cranial INS 420 and be used to smooth the transition between the skull and cranial INS 420. Accessory 422 may be formed into various shapes, sizes, and materials, e.g., silicone.

Figure 21:
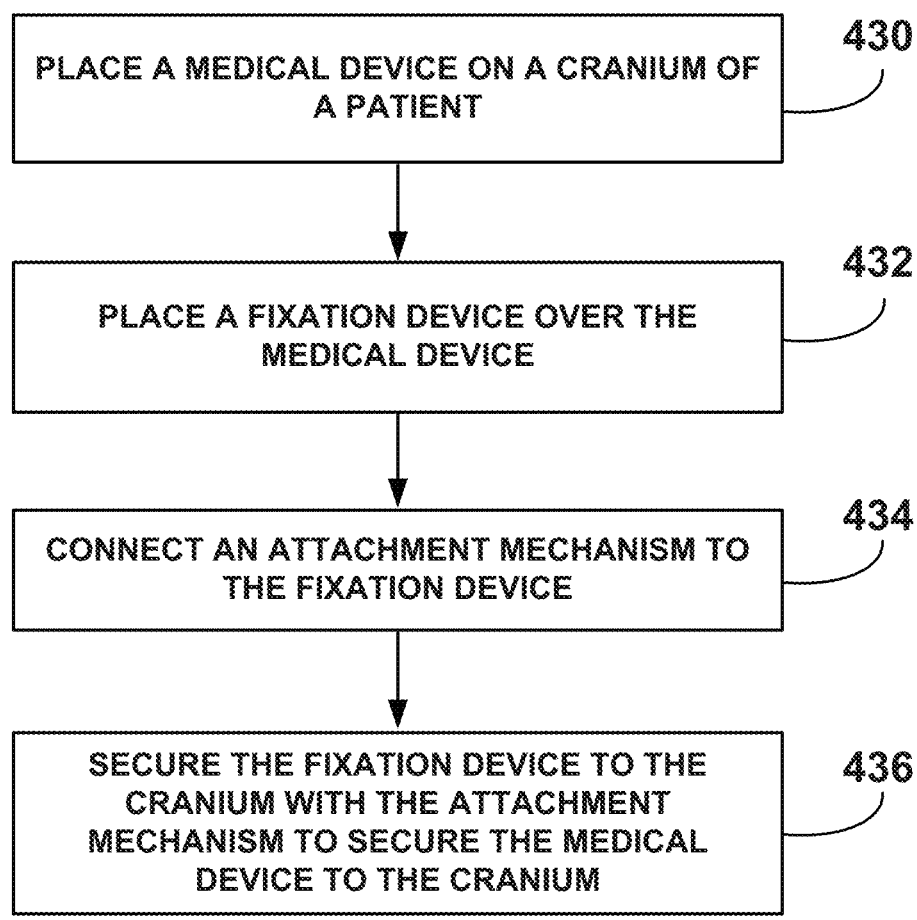
FIG. 21 is a flow diagram illustrating an example process, in accordance with one or more aspects of this disclosure.

FIG. 21 is a flow diagram illustrating an example process of securing a medical device with a fixation device, in accordance with one or more aspects of this disclosure. The technique of FIG. 21 will be described with concurrent reference to system 10 of FIG. 1A, although a person having ordinary skill in the art will understand that the technique may be performed by another system, and that system 10 may perform other techniques.

A clinician may place a medical device on a cranium of a patient (430). In some examples, a clinician may first create cranium recess 17 for the medical device, e.g., IMD 14, may be partially inserted in cranium 24. The clinician may form the cranium recess 17 with one or more tools, such as a bone drill. A clinician may also place a plurality of IMDs 14 on cranium 24. Once IMD 14 is placed on cranium 24, a clinician may place fixation device 12 over IMD 14 (432). Placing fixation device 12 over IMD 14 may include extending and stretching fixation device 12 over IMD 14. If there is more than one IMD 14, clinician may extend fixation device 12 over a plurality of IMDs 14. In other examples, a clinician may use a plurality of fixation devices 12 to secure a single IMD 14 or a plurality of IMDs 14. A clinician may stretch fixation device 12 over IMD 14 in one direction and attach a second fixation device 12 in the same or a different direction across IMD 14. For example, a first fixation device 12 and a second fixation device 12 may be attached to cranium 24 in a substantially orthogonal direction to one another. In some examples, the first and second fixation device 12 may be the same. Or, the first and second fixation device 12 may differ from each other, including differing by at least one of size, shape, or material. For example, a rectangular-shaped, first fixation device 12 may be relatively smaller and more flexible than an oval-shaped, second fixation device 12, which may be relatively larger and more rigid. Fixation devices 12 may be applied for different reasons. For example, a first fixation device 12 may provide coverage of IMD 14 from the external environment, and a second fixation device 12 may provide a biasing force to secure IMD 14 against cranium 24.

Once fixation device 12 is placed over IMD 14, an attachment mechanism, such as a bone screw, may be connected to fixation device 12 (434). For example, a bone screw may be inserted through an inner channel 40A of fixation device 12 similar to the example shown in FIG. 6A. In some examples, attachment mechanisms may be another mechanism besides a bone screw, e.g., staples or sutures. In other examples, an adhesive, such as bone cement, cyanoacrylate, or other material, may be used to secure fixation device 12 into place on cranium 26.

After attachment mechanism and fixation device 12 are connected, fixation device 12 may be secured to cranium 24 with the attachment mechanism (436). In some examples, if a recess was formed into cranium 24, bone cement may be filled in recess to help secure fixation device 12. In one example, the attachment mechanism may be bone screws, suturing directly to the surrounding tissue, suturing to mechanical components (e.g., anchors) that are secured (screwed) into cranium 24, securing with various types of straps (e.g., nonmetallic straps) that are screwed down, or the like. As discussed above, an attachment mechanism may be one or more bone screws inserted through a portion of fixation device 12 and secured to an exterior of cranium 24 of patient 26. In some examples, bone screws may provide fixation device 12 permanent attachment to cranium 24. Fixation device 12 may be constructed of a rigid material to IMD 14 secure over a long period of time. For example, fixation device 12 may secure IMD 14 on the order of years. In other examples, fixation device 12 may be bioabsorbable and cranium 24 may eventually secure IMD 14 without the need for fixation device 12.

In some examples, a technique for securing fixation device 12 and securing IMD 14 may include other, optional steps in addition to those shown in FIG. 21. For example, the technique of FIG. 21 may optionally include a clinician making an incision through the scalp of patient 26 and pulling back a resulting flap of skin to expose the desired area of cranium 24 before placing IMD 14 cranium 24 (430). In some examples, as discussed above, a clinician may make a recess in cranium 24 before placing IMD 14 on cranium 24.

The steps of technique of FIG. 21 may be rearranged. For example, the step of placing fixation device 12 over IMD 14 (432) may come after the step of connecting an attachment mechanism to fixation device 12 (434). In some examples, before placing fixation device 12 over IMD 14, an attachment mechanism, e.g., bone screws, may be inserted into fixation device 12. The technique of FIG. 21 may in some examples include using bone cement to secure fixation device 12 to cranium 24. In other examples, one or more bone screws may be used to secure fixation device 12 to cranium 24. A combination of bone cement and one or more bone screws may in some cases be used to secure fixation device 12 to cranium 24. The provided examples of rearranging the steps are not limiting and other steps may be rearranged, added, or removed when developing a technique to placing fixation device 12 over IMD 14 and securing IMD 14 to cranium 24.

The following examples are described herein. Example 1: a fixation device comprising: a flexible band comprising: a first base portion; a second base portion; and a connecting strap connecting the first base portion to the second base portion, the connecting strap configured to retain a medical device to an anatomical structure of a patient, wherein the flexible band is constructed of a first material; and a plurality of inserts, each insert of the plurality of inserts defining an inner channel and constructed of a second material more rigid than the first material of the flexible band, wherein a first insert of the plurality of inserts is at least partially within the first base portion, and wherein a second insert of the plurality of inserts is at least partially within the second base portion.

Example 2: the fixation device of example 1, wherein each insert of the plurality of inserts defines a conical recess that opens from the inner channel, the conical recess and the inner channel configured to receive a bone screw that secures the flexible band to a cranium of the patient.

Example 3: the fixation device of any of examples 1 or 2, wherein the flexible band comprises a standoff structure formed on the connecting strap, the standoff structure configured to contact the medical device and increase a fixation force between the flexible band and the medical device.

Example 4: the fixation device of example 3, wherein the standoff structure is constructed of the first material and disposed on a single side of the connecting strap.

Example 5: the fixation device of any of examples 1 through 4, wherein each insert of the plurality of inserts comprises one or more tabs, wherein the one or more tabs extend radially outward from an outer surface of each insert, and wherein the one or more tabs are configured to secure the respective insert within the flexible band.

Example 6: the fixation device of any of examples 1 through 5, wherein an elastic modulus of the first material is less than an elastic modulus of the second material.

Example 7: the fixation device of any of examples 1 through 6, wherein the first material comprises silicone, and wherein the second material comprises a rigid molded plastic.

Example 8: the fixation device of example 7, wherein the rigid molded plastic comprises nylon.

Example 9: the fixation device of any of examples 1 through 8, wherein each insert of the plurality of inserts defines a respective center axis, and wherein the respective center axis of the plurality of inserts are substantially parallel to one another.

Example 10: the fixation device of any of examples 1 through 9, wherein the first base portion and the second base portion each define a base thickness greater than a strap thickness of the connecting strap, and wherein elongation of the flexible band to retain the medical device occurs substantially in the connecting strap instead of the first base portion or the second base portion.

Example 11: the fixation system of example 10, wherein the strap thickness of the connecting strap is in the range from approximately 0.5 millimeters (mm) (20 thousandths of an inch (thou)) to approximately 1.5 mm (60 thou).

Example 12: the fixation system of any of examples 1 through 11, wherein at least one of the first material and second material comprises a biodegradable material.

Example 13: the fixation system of any of examples 1 through 12, wherein a cross-section of the connecting strap is less than a first cross-section of the first base portion and less than a second cross-section of the second base portion.

Example 14: the fixation system of any of examples 1 through 13, wherein the connecting strap, when stretched over the medical device, is biased to retain the medical device against the cranium.

Example 15: a fixation system comprising: a fixation device comprising: a flexible band comprising: a first base portion; a second base portion; and a connecting strap connecting the first base portion to the second base portion, the connecting strap configured to retain a medical device to an anatomical structure of a patient, wherein the flexible band is constructed of a first material; and a plurality of inserts, each insert of the plurality of inserts defining an inner channel and constructed of a second material more rigid than the first material of the flexible band, wherein a first insert of the plurality of inserts is at least partially within the first base portion, and wherein a second insert of the plurality of inserts is at least partially within the second base portion; and at least one attachment mechanism configured to attach the fixation device to a patient.

Example 16: the fixation system of example 15, wherein the at least one attachment mechanism comprises at least one of a staple, bone cement, and a bone screw, and wherein the at least one attachment mechanism is configured to attach the fixation device to a cranium of the patient.

Example 17: the fixation system of any of examples 15 or 16, wherein the fixation system comprises at least two fixation devices.

Example 18: the fixation system of example 17, wherein each of the at least two fixation devices are constructed of the same first material, and wherein each of the at least two fixation devices are constructed of the same second material.

Example 19: a method comprising: placing a medical device on a patient; extending a fixation device over the medical device, the fixation device comprising: a flexible band comprising: a first base portion; a second base portion; and a connecting strap connecting the first base portion to the second base portion, the connecting strap configured to retain a medical device to an anatomical structure of a patient, wherein the flexible band is constructed of a first material; and a plurality of inserts, each insert of the plurality of inserts defining an inner channel and constructed of a second material more rigid than the first material of the flexible band, wherein a first insert of the plurality of inserts is at least partially within the first base portion, and wherein a second insert of the plurality of inserts is at least partially within the second base portion; and securing the fixation device to the patient.

Example 20: the method of example 19, wherein the fixation device is a first fixation device, and wherein the method of example 19 further comprises: extending a second fixation device over the medical device; and securing the second fixation device to the patient.

Example 21: the method of any of examples 19 or 20, wherein securing the fixation device to the patient comprises securing the fixation device to a cranium of the patient.

Example 22: the method of any of examples 19 through 21, wherein extending the fixation device over the medical device comprises stretching the fixation device over the medical device.

It should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Various examples have been described. These and other examples are within the scope of the following claims.

What is claimed is:

1. A fixation device comprising:
   a flexible band configured to stretch over a medical device, the flexible band comprising:
   a first base portion;
   a second base portion; and
   a connecting strap between and connecting the first base portion to the second base portion, the connecting strap configured to retain the medical device to an anatomical structure of a patient, wherein the flexible band is constructed of a first material; and
   a plurality of inserts, each insert of the plurality of inserts defining an inner channel within the insert and constructed of a second material more rigid than the first material of the flexible band, wherein a first insert of the plurality of inserts is disposed at least partially within the first base portion, wherein a second insert of the plurality of inserts is disposed at least partially within the second base portion, and wherein each insert of the plurality of inserts is configured to accept a respective attachment mechanism within the inner channel, wherein each insert of the plurality of inserts defines a conical recess that opens from the inner channel, the conical recess and the inner channel configured to receive a bone screw that secures the flexible band to a cranium of the patient.

2. The fixation device of claim 1, wherein each insert of the plurality of inserts defines a conical recess that opens from the inner channel, the conical recess and the inner channel configured to receive a bone screw that secures the flexible band to a cranium of the patient wherein each insert of the plurality of inserts defines a conical recess that opens from the inner channel, the conical recess and the inner channel configured to receive a bone screw that secures the flexible band to a cranium of the patient, wherein the bone screw is the respective attachment mechanism.

3. The fixation device of claim 1, wherein the flexible band comprises a standoff structure formed on the connecting strap, the standoff structure configured to contact the medical device and increase a fixation force between the flexible band and the medical device.

4. The fixation device of claim 3, wherein the standoff structure is constructed of the first material and disposed on a single side of the connecting strap.

5. The fixation device of claim 1, wherein each insert of the plurality of inserts comprises one or more tabs, wherein the one or more tabs extend radially outward from an outer surface of each insert, and wherein the one or more tabs are configured to secure the respective insert within the flexible band.

6. The fixation device of claim 1, wherein an elastic modulus of the first material is less than an elastic modulus of the second material.

7. The fixation device of claim 1, wherein the first material comprises silicone, and wherein the second material comprises a rigid molded plastic.

8. The fixation device of claim 7, wherein the rigid molded plastic comprises nylon.

9. The fixation device of claim 1, wherein each insert of the plurality of inserts defines a respective center axis, and wherein the respective center axis of the plurality of inserts are substantially parallel to one another.

10. The fixation device of claim 1, wherein the first base portion and the second base portion each define a base thickness greater than a strap thickness of the connecting strap, and wherein elongation of the flexible band to retain the medical device occurs substantially in the connecting strap instead of the first base portion or the second base portion.

11. The fixation device of claim 10, wherein the strap thickness of the connecting strap is in the range from approximately 0.5 millimeters (mm) (20 thousandths of an inch (thou)) to approximately 1.5 mm (60 thou).

12. The fixation device of claim 1, wherein at least one of the first material and second material comprises a biodegradable material.

13. The fixation device of claim 1, wherein a cross-section area of the connecting strap is less than a first cross-section area of the first base portion and less than a second cross-section area of the second base portion.

14. The fixation device of claim 1, wherein the connecting strap is configured to, when stretched over the medical device, be biased to retain the medical device against the cranium.

15. A fixation system comprising:
    a fixation device comprising:
    a flexible band configured to stretch over a medical device, the flexible band comprising:
    a first base portion;
    a second base portion; and
    a connecting strap between and connecting the first base portion to the second base portion, the connecting strap configured to retain the medical device to an anatomical structure of a patient, wherein the flexible band is constructed of
    a first material; and
    a plurality of inserts, each insert of the plurality of inserts defining an inner channel within the insert and constructed of a second material more rigid than the first material of the flexible band, wherein a first insert of the plurality of inserts is disposed at least partially within the first base portion, wherein a second insert of the plurality of inserts is disposed at least partially within the second base portion, and wherein each insert of the plurality of inserts is configured to accept a respective attachment mechanism of a plurality of attachment mechanisms within the inner channel wherein each insert of the plurality of inserts comprises one or more tabs, wherein the one or more tabs extend radially outward from an outer surface of each insert, and wherein the one or more tabs are configured to secure the respective insert within the flexible band; and
    the plurality of attachment mechanisms configured to attach the fixation device to the patient.

16. The fixation system of claim 15, wherein the plurality of attachment mechanisms comprise at least one of a staple, bone cement, and a bone screw, and wherein the plurality of attachment mechanisms is configured to attach the fixation device to a cranium of the patient.

17. The fixation system of claim 15, wherein the fixation system comprises at least two fixation devices.

18. The fixation system of claim 17, wherein each of the at least two fixation devices are constructed of the same first material, and wherein each of the at least two fixation devices are constructed of the same second material.

19. A method comprising:
    placing a medical device on a patient;
    extending a fixation device over the medical device, the fixation device comprising:
    a flexible band configured to stretch over a medical device, the flexible band comprising:

a first base portion;

a second base portion; and a connecting strap between and connecting the first base portion to the second base portion, the connecting strap configured to retain the medical device to an anatomical structure of a patient, wherein the flexible band is constructed of a first material; and a plurality of inserts, each insert of the plurality of inserts defining an inner channel within the insert and constructed of a second material more rigid than the first material of the flexible band, wherein a first insert of the plurality of inserts is disposed at least partially within the first base portion, wherein a second insert of the plurality of inserts is disposed at least partially within the second base portion, and wherein each insert is configured to accept a respective attachment mechanism within the inner channel, wherein each insert of the plurality of inserts defines a conical recess that opens from the inner channel, the conical recess and the inner channel configured to receive a bone screw that secures the flexible band to a cranium of the patient; and securing the fixation device to the patient.

20. The method of claim 19, wherein the fixation device is a first fixation device, and wherein the method of claim 19 further comprises:

extending a second fixation device over the medical device; and securing the second fixation device to the patient.

21. The method of claim 19, wherein securing the fixation device to the patient comprises securing the fixation device to a cranium of the patient.

22. The method of claim 19, wherein extending the fixation device over the medical device comprises stretching the flexible band over the medical device.

* * * * *